(12) United States Patent
Özes

(10) Patent No.: US 10,364,230 B2
(45) Date of Patent: Jul. 30, 2019

(54) CHROMENE-2 DERIVATIVES AND USE THEREOF IN THE TREATMENT OF FIBROSIS

(71) Applicant: Osman Nidai Özes, Antalya (TR)

(72) Inventor: Osman Nidai Özes, Antalya (TR)

(73) Assignee: ALTAY THERAPEUTICS, INC., San Bruno, CA (US)

( * ) Notice: Subject to any disclaimer, the term of this patent is extended or adjusted under 35 U.S.C. 154(b) by 0 days.

(21) Appl. No.: 15/524,011

(22) PCT Filed: Apr. 17, 2015

(86) PCT No.: PCT/TR2015/000156
§ 371 (c)(1),
(2) Date: May 3, 2017

(87) PCT Pub. No.: WO2016/072946
PCT Pub. Date: May 12, 2016

(65) Prior Publication Data
US 2017/0313673 A1    Nov. 2, 2017

(30) Foreign Application Priority Data

Nov. 5, 2014  (TR) .............................. a 2014/12999

(51) Int. Cl.
*C07D 311/04* (2006.01)
*C07C 43/20* (2006.01)
*C07C 43/23* (2006.01)
*C07C 409/02* (2006.01)
*C07C 49/84* (2006.01)

(52) U.S. Cl.
CPC .......... *C07D 311/04* (2013.01); *C07C 43/202* (2013.01); *C07C 43/23* (2013.01); *C07C 49/84* (2013.01); *C07C 409/02* (2013.01)

(58) Field of Classification Search
None
See application file for complete search history.

(56) References Cited

FOREIGN PATENT DOCUMENTS

EP    2295053 A1    3/2011

OTHER PUBLICATIONS

International Search Report for corresponding International Application No. PCT/TR2015/000156.
Amanda Sanchez-Recillas et al: "Semisynthesis, ex vivo evaluation, and SAR studies of coumarin derivatives as potential antiasthmatic drugs", European Journal of Medicinal Chemistry, vol. 77, Apr. 1, 2014 (Apr. 1, 2014), pp. 400-408.

*Primary Examiner* — Heidi Reese
(74) *Attorney, Agent, or Firm* — Kilpatrick Townsend & Stockton LLP

(57) ABSTRACT

Disclosed are chromene-2 derivatives and the use thereof in the treatment of fibrosis. Specifically, disclosed are the derivatives of a compound having a main structure of 6,7-dimethoxy-chromenylium perchlorate (1) and pharmaceutical compositions, combinations and pharmaceutically suitable salts thereof for the treatment of fibrosis.

17 Claims, 19 Drawing Sheets

1 ←

2 ←

3 ←

4.5 ←

4.6 ←

4.7 ←

4.8 ←

4.9 ←

5.5 ←

5.6 ←

5.7 ←

5.8 ←

5.9 ←

6.5 ←

6.6

6.7 ←

6.8 ←

6.9 ←

7 ←

7.1 ←

7.2 ←

7.3 ←

7.4 ←

7.5

7.6

7.7

7.8

7.9

8 ←

8.1 ←

8.2 ←

8.3 ←

8.4 ←

8.5 ←

8.6 ←

8.7 ←

8.8 ←

8.9 ←

9 ←

9.1 ←

9.2 ←

9.3 ←

9.4 ←

9.5 ←

9.6 ←

9.7 ←

9.8 ←

9.9 ←

10.5 ←

10.6 ←

10.7 ←

10.8 ←

10.9 ←

11 ←

11.1 ←

11.2 ←

11.3 ←

11.4 ←

11.5 ←

11.6 ←

11.7 ←

11.8 ←

11.9 ←

CHROMENE-2 DERIVATIVES AND USE THEREOF IN THE TREATMENT OF FIBROSIS

CROSS-REFERENCE TO RELATED APPLICATIONS

The present application is a 35 U.S.C. § 371 national stage entry of International Patent Application No. PCT/TR2015/000156, filed Apr. 17, 2015, which claims priority to Turkish Patent Application No. TR20140012999, filed Nov. 5, 2014; which applications are incorporated herein by reference in their entirety.

FIELD OF THE INVENTION

The present invention is related to chromene-2 derivatives and use thereof in the treatment of fibrosis. The invention is related to the derivatives of a compound having a main structure of 6,7-dimethoxy-chromenylium perchlorate (1) and pharmaceutical compositions, combinations and pharmaceutically suitable salts thereof for the treatment of fibrosis.

The R1 and R2 positions are selected as main replacement positions and these points are combined with hydroxyl (—OH), methyl (—CH3), ethyl (—C2H5) and combinations thereof.

The compounds of this invention have the ability to affect the TGF☐ signal transduction pathways for synthesis of collagen, elastin, fibronectin, COMP (Cartilage Oligomeric Protein). Osteopontin etc, and inhibit epithelial mesenchimal cell transition. Thus, said compounds can be effectively used in the treatment of idiopathic pulmonary fibrosis-IPF, Chronic Obstructive Pulmonary Disease (COPD), sarcoidosis, kidney fibrosis, heart fibrosis, atherosclerosis, pancreatic fibrosis, pancreatitis, liver fibrosis and cirrhosis, non-alcoholic steatohepatitis-NASH) and alcoholic siteatohepatitis Lung fibrosis is a disease with an unknown etiology. Although multiple factors have been blamed for development of IPF actual cause for development of IPF is unknown. Since its cause is unknown it is named as idiopathic lung fibrosis. IPF is commonly accepted as a disease of elderly, and its prevalence is 20/100,000 for men and 13/100,000 for women. Currently, it is estimated that 5 million people are affected from this disease worldwide (Eric B Meltzer and Paul W Noble Idiopathic pulmonary fibrosis. *Orphanet Journal of Rare Diseases* 2008, 3:8:1-15). It is commonly accepted that growth factors and cytokine, which are secreted by macrophages accumulate in the lung as a response to inflammation, play significant role in development of IPF (Todd N W, Scheraga R G, Galvin J R, Iacono A T, Britt E J, Luzina I G, et al. Lymphocyte aggregates persist and accumulate in the lungs of patients with idiopathic pulmonary fibrosis. J Inflamm Res 2013; 6: 63-70.) Cytokines IL4, IL13 and TGF☐ secreted by macrophages initiates EMT process and during which alveolar epithelia cells turn mesenchima fibroblasts, (Kim K K, Kugler M C, Wolters P J, Robillard L, Galvez M G, Brumwell A N. et al. Alveolar epithelial cell mesenchymal transition develops in vivo during pulmonary fibrosis and is regulated by the extracellular matrix. Proc Natl Acad Sci USA 2006; 103: 13180-1318. Konigshoff M. Lung cancer in pulmonary fibrosis: tales of epithelial cell plasticity. Respiration 2011; 81: 353-358). Among the secreted cytokines TGFb induces expression and deposition of collagen from alveolar epithelial cells. (Broekelmann T J, Limper A H, Colby T V, McDonald J A. Transforming growth factor beta 1 is present at sites of extracellular matrix gene expression in human pulmonary fibrosis. Proc Natl Acad Sci USA 1991:88:6642-6646. Khalil N, O'Connor R N, Flanders K C, Unruh H. TGF-b1, but not TGF-b2 or TGF-b3, is differentially present in epithelial cells of advanced pulmonary fibrosis: an immunohistochemical study. *Am J Respir Cell Mol Biol* 1996; 14:131-138). Structural proteins deposited at extracellular matrix reduces the size of alveolar space, limits diffusion of oxygen and make breathing impossible. (Zhang K, Rekhter M D, Gordon D, Phan S H, Myofibroblasts and their role in lung collagen gene expression during pulmonary fibrosis: a combined immunohistochemical and in situ hybridization study. *Am J Pathol* 1994; 145:114-125. Turner-Warwick M, Burrows B, Johnson A: Cryptogenic fibrosing alveolitis: clinical features and their influence on survival. *Thorax* 1980, 35(3):171-180. Agusti A G, Roca J, Gea J, Wagner P D, Xaubet A, Rodriguez-Roisin R: Mechanisms of gas-exchange impairment in idiopathic pulmonary fibrosis. *Am Rev Respir Dis* 1991, 143(2):219-225). Uncontrolled growth of lung cells and deposition of matrix proteins perturbs the structure of lung which can be visualized by computerised tomography (CT). According to the results obtained from CT scans, one of the hallmark of lung fibrosis is the formation of "honey comb" structures, and this is "gold standard" in defining this disease. (Parambil J G, Myers J L, Ryu J H: Histopathologic features and outcome of patients with acute exacerbation of idiopathic pulmonary fibrosis undergoing surgical lung biopsy. *Chest* 2005, 128 (5):3310-3315. Akira M, Hamada H, Sakatani M, Kobayashi C, Nishioka M. Yamamoto S: CT findings during phase of accelerated deterioration in patients with idiopathic pulmonary fibrosis. *AJR Am J Roentgenol* 1997, 168(1):79-83).

Since lung fibrosis was initially thought to develop as a result of inflammation it was treated with anti-inflammatory compounds such as prednisol, n-acetyl cystein, cyclophosphamide, and cortisol. However, none of these treatment options produced significant survival benefit for IPF patients. (Collard H R, Ryu J H, Douglas W W, Schwarz M I, Curran-Everett D. King T E Jr., Brown K K: Combined corticosteroid and cyclophosphamide therapy does not alter survival in idiopathic pulmonary fibrosis. *Chest* 2004, 125 (6):2169-2174. Behr J, Maier K, Degenkolb B. Krombach F, Vogelmeier C: Antioxidative and clinical effects of high-dose N-acetylcysteine in fibrosing alveolitis. Adjunctive therapy to maintenance immunosuppression. *Am J Respir Crit Care Med* 1997, 156(6):1897-1901. Zisman D A, Lynch J P 3rd, Toews G B, Kazerooni E A, Flint A, Martinez F J: Cyclophosphamide in the treatment of idiopathic pulmonary fibrosis: a prospective study in patients who failed to respond to corticosteroids. *Chest* 2000, 117(6):1619-1626). At the beginning of 2000, small molecule named "Pirfenidone" was tested against IPF in USA and Japan. In 2008, a japanese company Shinogi completed a successful phase III study and got approval for the use Pirfenidone to treat IPF patients in Japan. (Azuma A, Nukiwa T, Tsuboi E. et al. Double-blind, placebo-controlled, trial of pirfenidone in patients with idiopathic pulmonary fibrosis. Am J Respir Crit Care Med 2005; 171:1040-1047). In addition to this, US company called InterMune conducted 3 independent phase 3 studies and showed the efficacy of this compound against IPF and got FDA approval in October of 2014, and began marketing Pirfenidone under the brand name Esbriest. Also, in October 2014, another novel drug "Nintedanib" produced by Boehringer Ingelheim (BI) got approval for IPF (Jason Potts, Dinesh Yogaratnam. Pirfenidone: A Novel Agent for the Treatment of Idiopathic Pulmonary Fibrosis *The Annals* of *Pharmacotherapy* n 2013 March, Volume 47 361-367, and InterMune and BI Web sites).

Currently, the only treatment options for IPF are Pirfenidone and Nintedanib and both drugs have limited efficacy. One of the main reasons for having difficulty to treat this disease is the fact that factor(s) causing the development of this disease are not fully understood. For this very reason, we believe that there is still need for development of new drug candidates to effective treatment of IPF.

In this respect, there are some patents or patent applications claiming the use of Chromene derivatives as an alternative treatment options. Some of these are shown below;

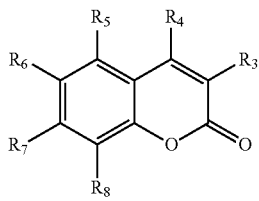

EP2295053A1 discloses Chromene and some of its derivatives generated by changing R1 and R2 have been claimed for treatment of fibrosis.

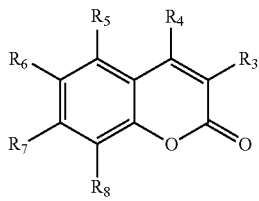

U.S. Pat. No. 8,048,912,B2 discloses the compound created from Chromene has been claimed to be used against fibrosis caused by TGF-beta.

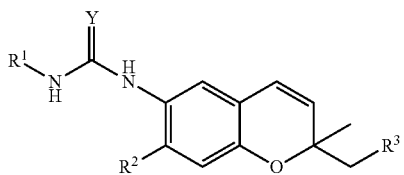

US 2009/0088477 A1 discloses the main structure shown below and its derivatives have been claimed to be used against asthma, COPD and atherosclerosis.

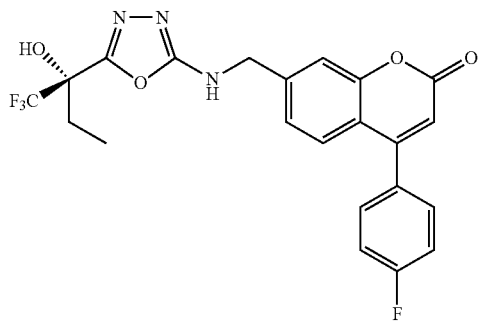 [SMILES: CC[C@](O)(c1nnc(NCc2ccc3c(-c4ccc(F)cc4)cc(=O)oc3c2)o1)C(F)(F)F]

WO 2006 070984 discloses the main structure shown below and its derivatives have been claimed to be used against diseases which derive from collagen deposition.

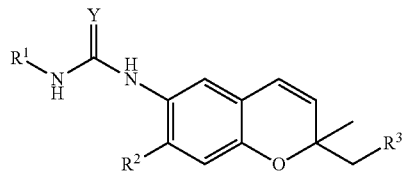

US 2012/0196867 A1 discloses the main structure shown below and its has been claimed to be used against COPD as phosphodiesterase inhibitor.

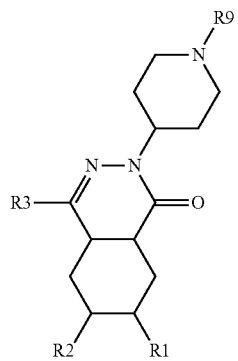

EP2620443A1 discloses the main structure shown below and its derivatives have been claimed to be used against fibrosis as Galectin-3 inhibitor.

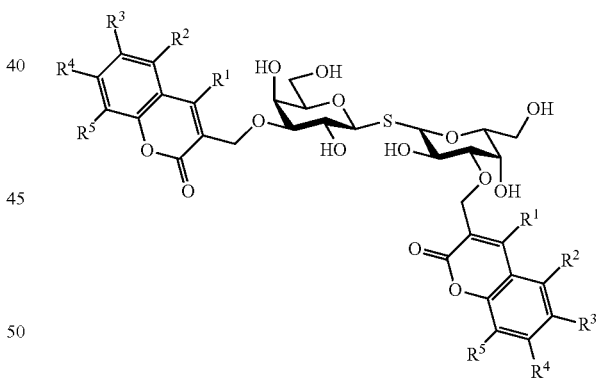

WO2006070984A1 discloses the main structure shown below and its derivatives have been claimed to be used against fibroplasias and TGF-induced fibrosis.

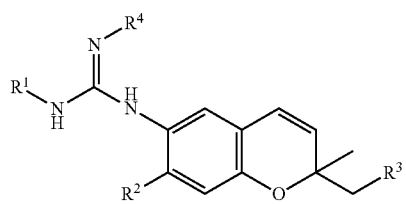

OBJECT OF THE INVENTION

Although derivatives of 6,7-dimethoxy 2H-chromen-2-one (1) have been claimed to be used as anti-fibrotic agent, currently there is no chromene-derived anti-fibrotic drugs. In the present invention, carbonyl oxygen is removed from Chromene structure, this yielded positively charged chromene, then from this structure, 72 different molecules composed of 8 different molecule (4,5,6,7,8,9,10,11) with 9 different combinations were generated.

EXPLANATION OF REFERENCES OF FIGURES

Figure 4:
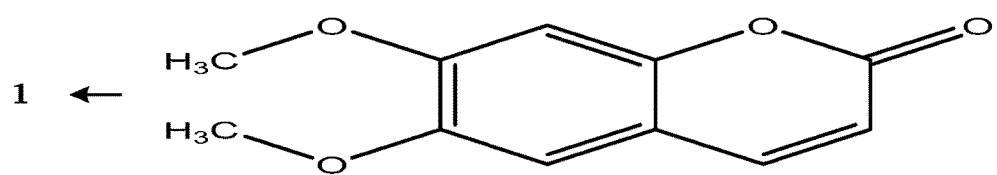
FIG. 4: 6,7-dimethoxy-2H-chromen-2-one

1: 6,7-dimethoxy-2H-chromen-2-one
2: Main compound produced from 6,7-dimethoxy-2H-chromen-2-one
3: Side chain added to the compound described at FIG. 5
4: First structure produced from FIG. 5.
4.1: 6,7-dimethoxy-chromenylium perchlorate
4.2: 6-ethoxy-7 methoxy 2,3,4,5,8-pentamethyl naphatehalen-1-ylium
4.3: 7-ethoxy-6-methoxy-2,3,4,5,8-pentamethyl naphatehalen-1-ylium
4.4: 6,7-diethoxy-2,3,4,5,8-pentamethyl naphatehalen-1-ylium
4.5: 6-hydroperoxy-7-methoxy-2,3,4,5,8-pentamethyl-naphatehalen-1-ylium
4.6: 7-hydroperoxy-6-methoxy-2,3,4,5,8-pentamethyl-naphatehalen-1-ylium
4.7: 6,7-dihydroperoxy-2,3,4,5,8-pentamethylnaphatehalen-1-ylium
4.8: 7-ethoxy-6-hydroperoxy-2,3,4,5,8-pentamethyl-naphatehalen-1-ylium
4.9: 6-ethoxy-7-hydroperoxy-2,3,4,5,8-pentamethyl-naphatehalen-1-ylium
5: Second structure produced from FIG. 5.

Figure 5:
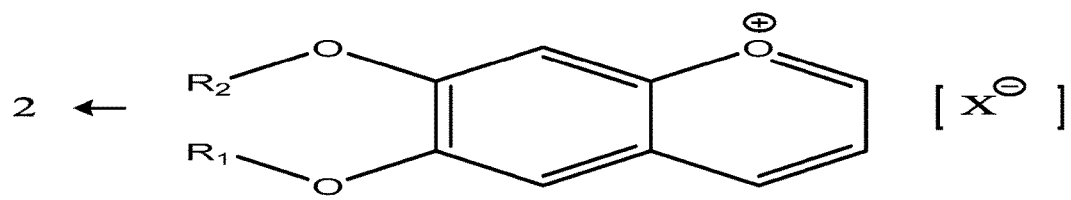
FIG. 5: Main compound produced from 6,7-dimethoxy-2H-chromen-2-one
Figure 6:
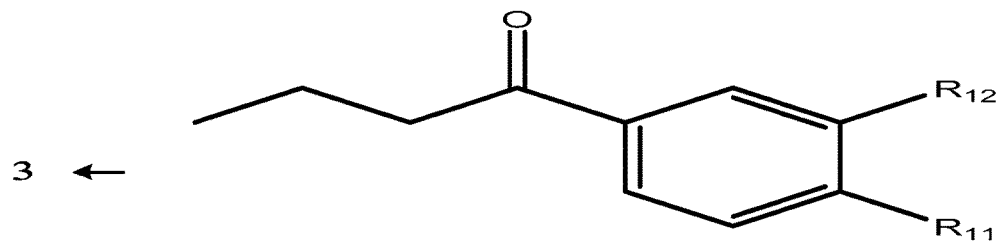
FIG. 6: Side chain added to the compound described at FIG. 5, FIG. 7: First structure produced from FIG. 5.
Figure 7:
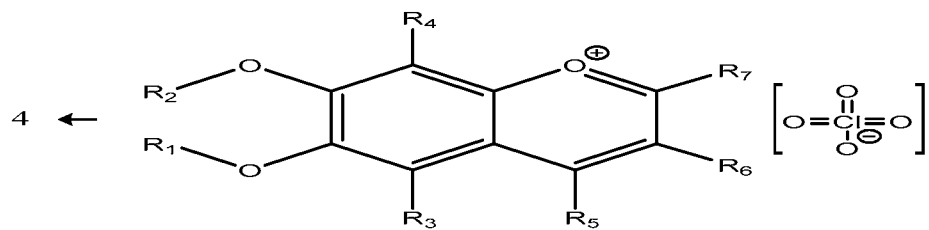
Figure 8:
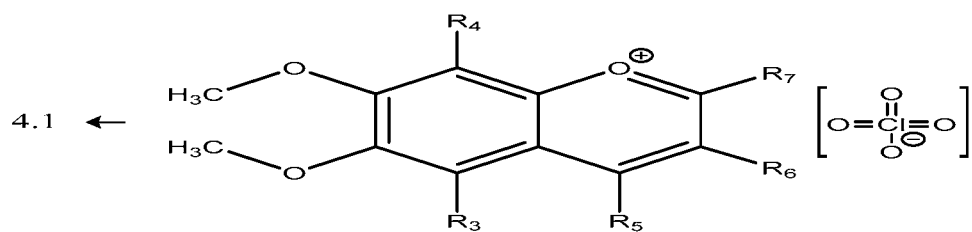
FIG. 8: 6,7-dimethoxy-chromenylium perchlorate.
Figure 9:
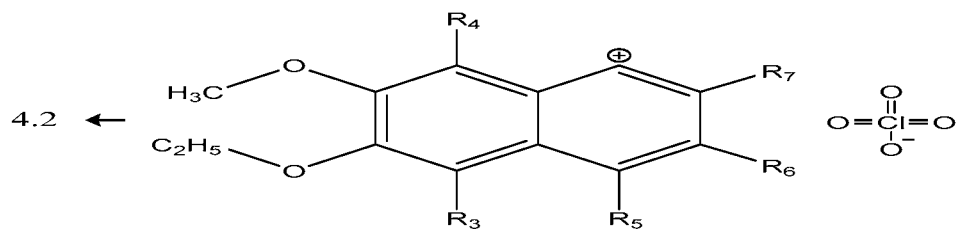
FIG. 9: 6-ethoxy-7 methoxy 2,3,4,5,8-pentamethyl naphatehalen-1-ylium
Figure 10:
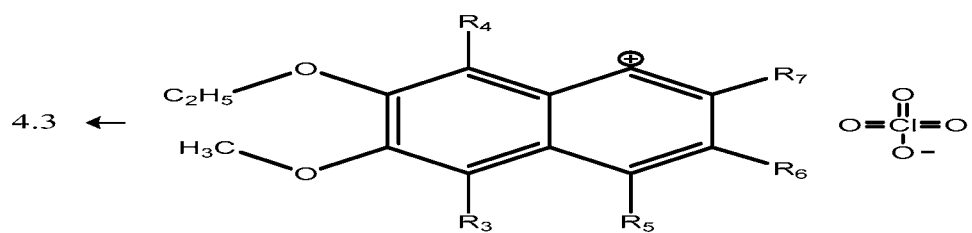
FIG. 10: 7-ethoxy-6-methoxy-2,3,4,5,8-pentamethyl naphatehalen-1-ylium.

5.1: 2-(4-(3,4-dimethoxy-2,5,6-trimethylphenyl)butan-2-yl)-6,7-dimethoxy-3,4,5,8-tetramethyl-1$\lambda^3$-chromen-(1:1) formaldehyde compound 5.2: 2-(4-(3,4-dimethoxy-2,5,6-trimethylphenyl)butan-2-yl)-6-ethoxy-7-methoxy-3,4,5,8-tetramethyl-1$\lambda^3$-chromen-(1:1) formaldehyde compound 5.3: 2-(4-(3,4-dimethoxy-2,5,6-trimethylphenyl)butan-2-yl)-7-ethoxy-6-methoxy-3,4,5,8-tetramethyl-1$\lambda^3$-chromen-(1:1) formaldehyde compound 5.4: 2-(4-(3,4-dimethoxy-2,5,6-trimethylphenyl)butan-2-yl)-6,7-diethoxy-3,4,5,8-tetramethyl-1$\lambda^3$-chromen-(1:1) formaldehyde compound 5.5: 2-(4-(3,4-dimethoxy-2,5,6-trimethylphenyl)butan-2-yl)-6-hydroperoxy-7-methoxy-3,4,5,8-tetramethyl-1$\lambda^3$-chromen (1:1) formaldehyde compound 5.6: 2-(4-(3,4-dimethoxy-2,5,6-trimethylphenyl)butan-2-yl)-7-hydroperoxy-6-methoxy-3,4,5,8-tetramethyl-1$\lambda^3$-chromen (1:1) formaldehyde compound 5.7: 2-(4-(3,4-dimethoxy-2,5,6-trimethylphenyl)butan-2-yl)-6,7-dihydroperoxy-3,4,5,8-tetramethyl-1$\lambda^3$-chromen (1:1) formaldehyde compound 5.8: 2-(4-(3,4-dimethoxy-2,5,6-trimethylphenyl)butan-2-yl)-7-ethoxy-6-hydroperoxy-3,4,5,8-tetramethyl-1$\lambda^3$-chromen (1:1) formaldehyde compound 5.9: 2-(4-(3,4-dimethoxy-2,5,6-trimethylphenyl)butan-2-yl)-6-ethoxy-7-hydroperoxy-3,4,5,8-tetramethyl-1$\lambda^3$-chromen (1:1) formaldehyde compound 6: 3th structure produced from FIG. 5.

6.1: 7-ethoxy-6methoxy-2,3,4,5,8-pentamethylnaphthalen-1-ylium 6.2: 6,7-diethoxy-2,3,4,5,8-pentamethyl naphatehalen-1-ylium 6.3: 6-methoxy-2,3,4,5,8-pentamethyl-7-propoxynaphatehalen-1-ylium 6.4: 6-ethoxy-2,3,4,5,8-pentamethyl-7-propoxynaphatehalen-1-ylium 6.5: 7-ethoxy-6-hydroperoxy-2,3,4,5,8-pentamethyl naphatehalen-1-ylium 6.6: 7-(hydroxymethoxy)-6-methoxy-2,3,4,5,8-pentamethyl naphatehalen-1-ylium 6.7: 6-hydroperoxy-7-(hydroxymethoxy)-2,3,4,5,8-pentamethyl naphatehalen-1-ylium 6.8: 6-hydroperoxy-2,3,4,5,8-pentamethyl-7-propoxynaphatehalen-1-ylium 6.9: 6-ethoxy-7-(hydroxymethoxy)-2,3,4,5,8-pentamethyl-naphatehalen-1-ylium 7: 4th structure produced from FIG. 5

7.1: 2-(4-(3,4-dimethoxy-2,5,6-trimethylphenyl)butan-2-yl)-7-ethoxy-6-methoxy-3,4,5,8-tetramethyl-1$\lambda^3$-chromen and methyl-$\lambda^1$-oxidane (4:1:1) formaldehyde compound 7.2: 2-(4-(3,4-dimethoxy-2,5,6-trimethylphenyl)butan-2-yl)-6,7-diethoxy-3,4,5,8-tetramethyl-1$\lambda^3$-chromen and methyl-$\lambda^1$-oxidane (3:1:1) formaldehyde compound 7.3: 2-(4-(3,4-dimethoxy-2,5,6-trimethylphenyl)butan-2-yl)-6-methoxy-3,4,5,8-tetramethyl-7-propoxy-1$\lambda^3$-chromen and methyl-$\lambda^1$-oxidane (3:1:1) formaldehyde compound 7.4: 2-(4-(3,4-dimethoxy-2,5,6-trimethylphenyl)butan-2-yl)-6-ethoxy-3,4,5,8-tetramethyl-7-propoxy-1$\lambda^3$-chromen and methyl-$\lambda^1$-oxidane (3:1:1) formaldehyde compound 7.5: 2-(4-(3,4-dimethoxy-2,5,6-trimethylphenyl)butan-2-yl)-7-ethoxy-6-hydroperoxy-3,4,5,8-tetramethyl-1$\lambda^3$-chromen and methyl-$\lambda^1$-oxidane (3:1:1) formaldehyde compound 7.6: 2-(4-(3,4-dimethoxy-2,5,6-trimethylphenyl)butan-2-yl)-6-methoxy-3,4,5,8-tetramethyl-1$\lambda^3$-chromen-7-yl)oxy)methanol and methyl-$\lambda^1$-oxidane (3:1:1) formaldehyde compound 7.7: 2-(4-(3,4-dimethoxy-2,5,6-trimethylphenyl)butan-2-yl)-6-hydroperoxy-3,4,5,8-tetramethyl-1$\lambda^3$-chromen-7-yl)oxy)methanol and methyl-$\lambda^1$-oxidane (3:1:1) formaldehyde compound 7.8: 2-(4-(3,4-dimethoxy-2,5,6-trimethylphenyl)butan-2-yl)-6-hydroperoxy-3,4,5,8-tetramethyl-7-propoxy-1$\lambda^3$-chromen and methyl $\lambda^1$-oxidane (3:1:1) formaldehyde compound 7.9: 2-(4-(3,4-dimethoxy-2,5,6-trimethylphenyl)butan-2-yl)-6-ethoxy-3,4,5,8-tetramethyl-1$\lambda^3$-chromen-7-yl)oxy)methanol and methyl-$\lambda^1$-oxidane (3:1:1) formaldehyde compound 8: 5th structure produced from FIG. 5.

8.1: 6-ethoxy 7-methoxy-2,3,4,5,8-pentamethylnaphatehalen-1-ylium 8.2: 7-methoxy-2,3,4,5,8-pentamethyl-6-propoxynaphatehalen-1-ylium 8.3: 6,7-diethoxy-2,3,4,5,8-pentamethylnaphatehalen-1-ylium 8.4: 7-ethoxy-2,3,4,5,8-pentamethyl-6-propoxynaphatehalen-1-ylium 8.5: 6-(hydroxymethoxy)-7-methoxy-2,3,4,5,8-pentamethylnaphatehalen-1-ylium 8.6: 6-ethoxy-7-hydroperoxy-2,3,4,5,8-pentamethyl-naphatehalen-1-ylium 8.7: 7-hydroperoxy-6-(hydroxymethoxy)-2,3,4,5,8-pentamethylnaphatehalen-1-ylium 8.8: 7-ethoxy-6-(hydroxymethoxy)-2,3,4,5,8-pentamethyl-naphatehalen-1-ylium 8.9: 7-hydroperoxy-2,3,4,5,8-pentamethyl-6-propoxynaphatehalen-1-ylium 9: 6th structure produced from FIG. 5.

9.1: 1-(3,4-dimethoxy-2,5,6-trimethylphenyl)-3-(6-ethoxy-7-methoxy-3,4,5,8-tetramethyl-1$\lambda^3$-chromen-2-yl)butan-1-one and methyl $\lambda^1$-oxidane (3:1:1) formaldehyde compound 9.2: 3-(6,7-diethoxy-3,4,5,8-tetramethyl-1$\lambda^3$-chromen-2-yl)-1-(3,4-dimethoxy-2,5,6-trimethylphenyl)butan-1-one and methyl-$\lambda^1$-oxidane (3:1:1) formaldehyde compound 9.3: 1-(3,4-dimethoxy-2,5,6-trimethylphenyl)-3-(7-methoxy-3,4,5,8-tetramethyl-6-propoxy-1$\lambda^3$-chromen-2-yl)butan-1-one and methyl $\lambda^1$-oxidane (3:1:1) formaldehyde compound 9.4: 1-(3,4-dimethoxy-2,5,6-trimethylphenyl)-3-(7-ethoxy-3,4,5,8-tetramethyl-6-propoxy-1$\lambda^3$-chromen-2-yl)butan-1-one and methyl $\lambda^1$-oxidane (3:1:1) formaldehyde compound 9.5: 1-(3,4-dimethoxy-2,5,6-trimethylphenyl)-3-(6-(hydroxymethoxy)-7-methoxy-3,4,5,8-tetramethyl-1$\lambda^3$-chromen-2-yl)butan-1-one and methyl $\lambda^1$-oxidane (3:1:1) formaldehyde compound 9.6: 1-(3,4-dimethoxy-2,5,6-trimethylphenyl)-3-(6-ethoxy-7-hydroperoxy-3,4,5,8-tetramethyl-1$\lambda^3$-chromen-2-yl) butan-1-one- and methyl-$\lambda^1$-oxidane (3:1:1) formaldehyde compound 9.7: 1-(3,4-dimethoxy-2,5,6-trimethylphenyl)-3-(7-hydroperoxy-6-(hydroxyperoxy)-3,4,5,8-tetramethyl-1$\lambda^3$-chromen-2-yl)butan-1-one and methyl-$\lambda^1$-oxidane (3:1:1) formaldehyde compound 9.8: 1-(3,4-dimethoxy-2,5,6-trimethylphenyl)-3-(7-ethoxy-6-(hydroxyperoxy)-3,4,5,8-tetramethyl-1$\lambda^3$-chromen-2-yl)butan-1-one and methyl $\lambda^1$-oxidane (3:1:1) formaldehyde compound 9.9: 1-(3,4-dimethoxy-2,5,6-trimethylphenyl)-3-(7-hydroperoxy-3,4,5,8-tetramethyl-6-propoxy-1λ³-chromen-2-yl)butan-1-one and methyl λ¹-oxidane (3:1:1) formaldehyde compound 10: 7th structure produced from FIG. 5.

Figure 11:
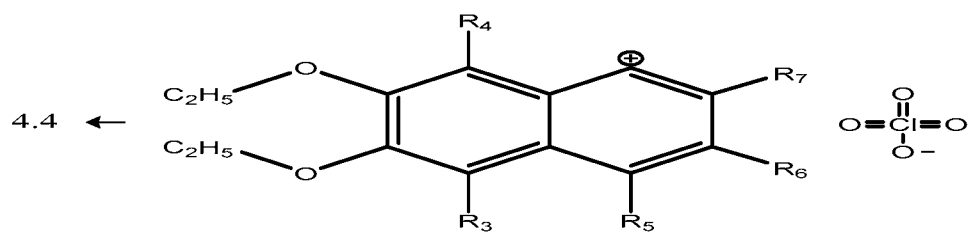
FIG. 11: 6,7-diethoxy-2,3,4,5,8-pentamethyl naphatehalen-1-ylium.
Figure 12:
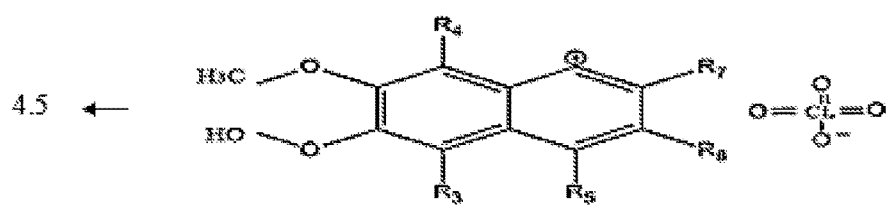
FIG. 12: 6-hydroperoxy-7-methoxy-2,3,4,5,8-pentamethylnaphatehalen-1-ylium
Figure 13:
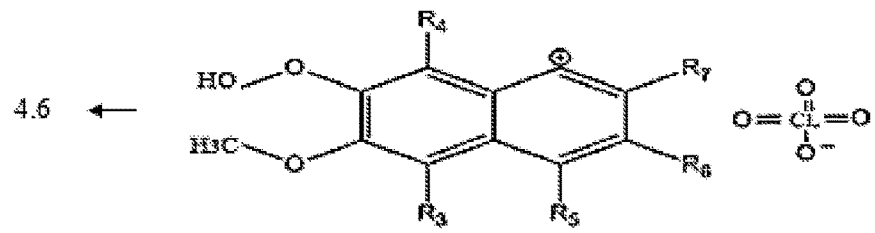
FIG. 13: 7-hydroperoxy-6-methoxy-2,3,4,5,8-pentamethylnaphatehalen-1-ylium
Figure 14:
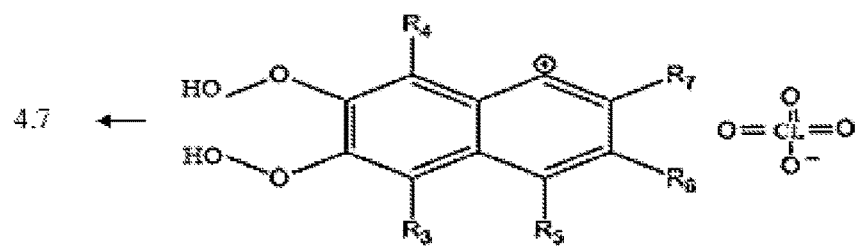
FIG. 14: 6,7-dihydroperoxy-2,3,4,5,8-pentamethyl-naphatehalen-1-ylium
Figure 15:
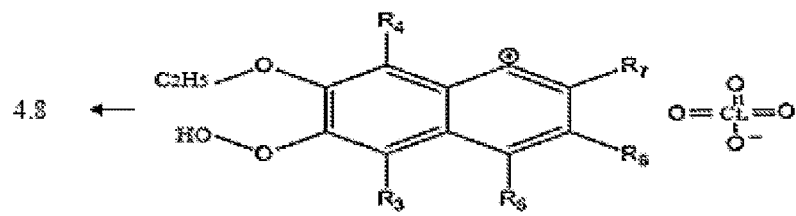
FIG. 15: 7-ethoxy-6-hydroperoxy-2,3,4,5,8-pentamethyl-naphatehalen-1-ylium
Figure 16:
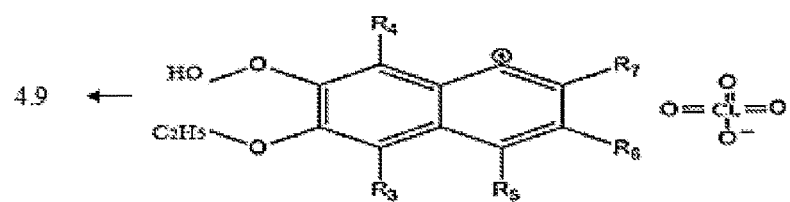
FIG. 16: 6-ethoxy-7-hydroperoxy-2,3,4,5,8-pentamethyl-naphatehalen-1-ylium
Figure 17:
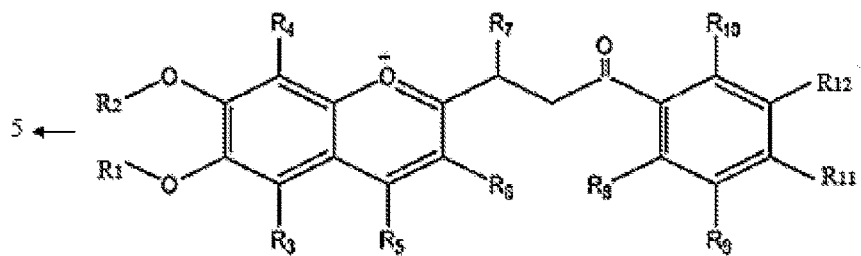
FIG. 17: Second structure produced from FIG. 5.
Figure 18:
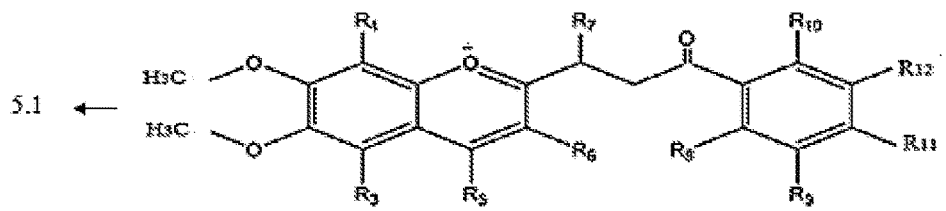
FIG. 18: 2-(4-(3,4-dimethoxy-2,5,6-trimethylphenyl)butan-2-yl)-6,7-dimethoxy-3,4,5,8-tetramethyl-1$\lambda^3$-chromen-(1:1) formaldehyde compound
Figure 19:
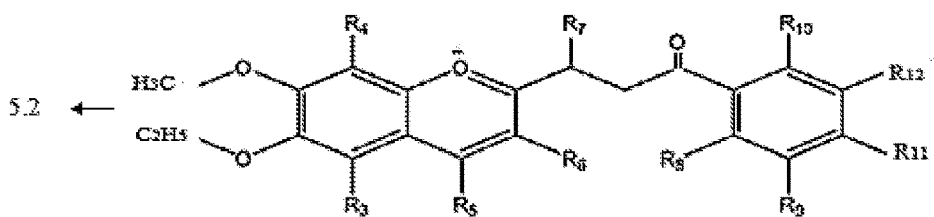
FIG. 19: 2-(4-(3,4-dimethoxy-2,5,6-trimethylphenyl)butan-2-yl)-6-ethoxy-7-methoxy-3,4,5,8-tetramethyl-1$\lambda^3$-chromen-(1:1) formaldehyde compound
Figure 20:
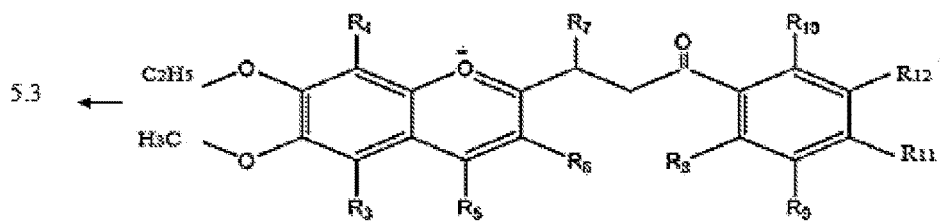
FIG. 20: 2-(4-(3,4-dimethoxy-2,5,6-trimethylphenyl)butan-2-yl)-7-ethoxy-6-methoxy-3,4,5,8-tetramethyl-1$\lambda^3$-chromen-(1:1) formaldehyde compound
Figure 21:
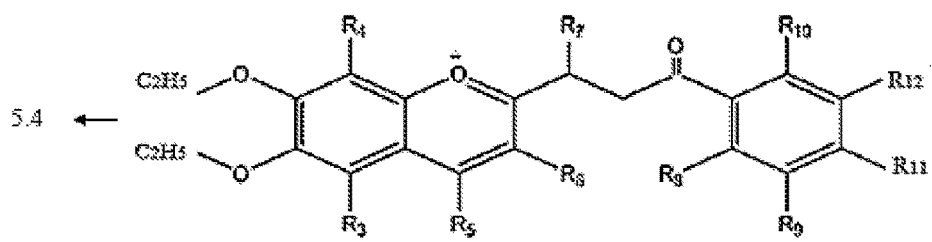
FIG. 21: 2-(4-(3,4-dimethoxy-2,5,6-trimethylphenyl)butan-2-yl)-6,7-diethoxy-3,4,5,8-tetramethyl-1$\lambda^3$-chromen-(1:1) formaldehyde compound
Figure 22:
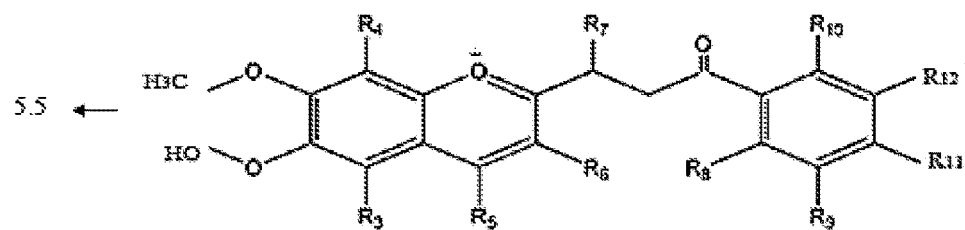
FIG. 22: 2-(4-(3,4-dimethoxy-2,5,6-trimethylphenyl)butan-2-yl)-6-hydroperoxy-7-methoxy-3,4,5,8-tetramethyl-1$\lambda^3$-chromen (1:1) formaldehyde compound
Figure 23:
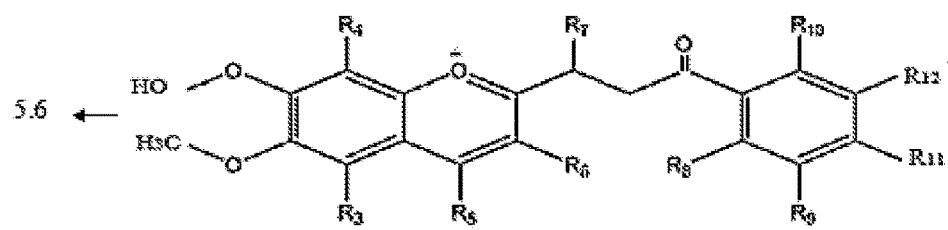
FIG. 23: 2-(4-(3,4-dimethoxy-2,5,6-trimethylphenyl)butan-2-yl)-7-hydroperoxy-6-methoxy-3,4,5,8-tetramethyl-1$\lambda^3$-chromen (1:1) formaldehyde compound
Figure 24:
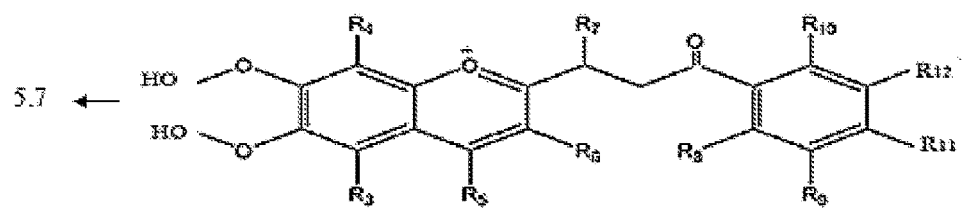
FIG. 24: 2-(4-(3,4-dimethoxy-2,5,6-trimethylphenyl)butan-2-yl)-6,7-dihydroperoxy-3,4,5,8-tetramethyl-1$\lambda^3$-chromen (1:1) formaldehyde compound
Figure 25:
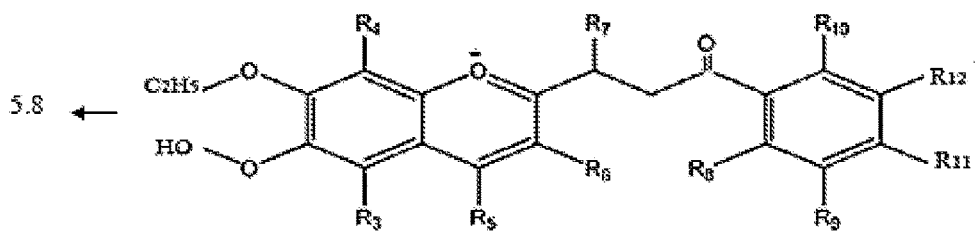
FIG. 25: 2-(4-(3,4-dimethoxy-2,5,6-trimethylphenyl)butan-2-yl)-7-ethoxy-6-hydroperoxy-3,4,5,8-tetramethyl-1$\lambda^3$-chromen (1:1) formaldehyde compound
Figure 26:
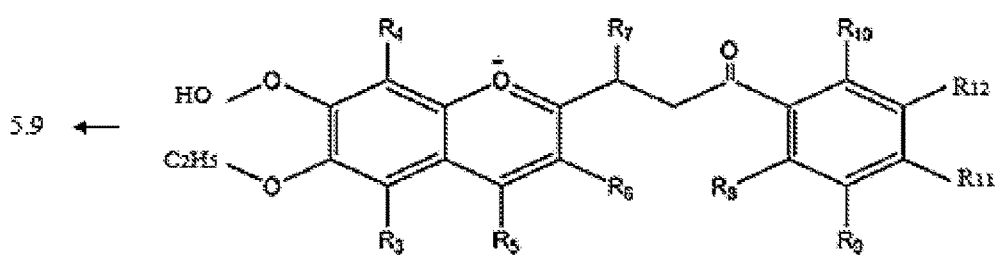
FIG. 26: 2-(4-(3,4-dimethoxy-2,5,6-trimethylphenyl)butan-2-yl)-6-ethoxy-7-hydroperoxy-3,4,5,8-tetramethyl-1$\lambda^3$-chromen (1:1) formaldehyde compound
Figure 27:
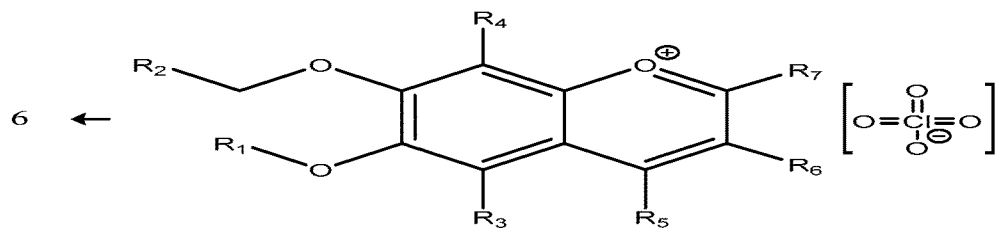
FIG. 27: 3th structure produced from FIG. 5.
Figure 28:
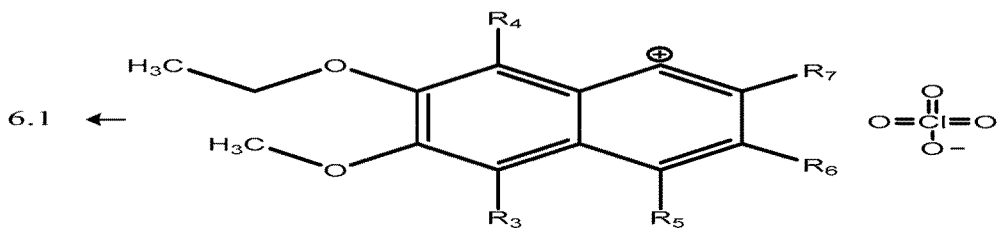
FIG. 28: 7-ethoxy-6methoxy-2,3,4,5,8-pentamethylnaphthalen-1-ylium
Figure 29:
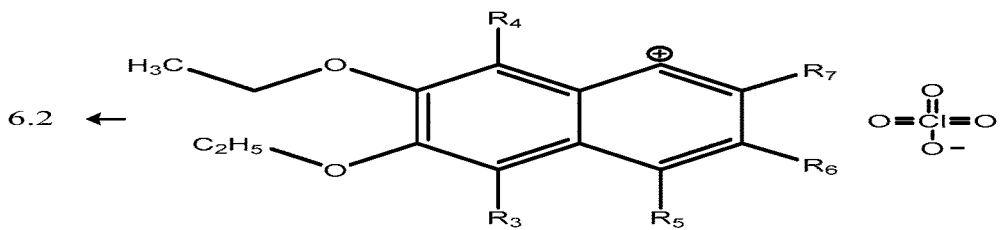
FIG. 29: 6,7-diethoxy-2,3,4,5,8-pentamethyl naphatehalen-1-ylium
Figure 30:
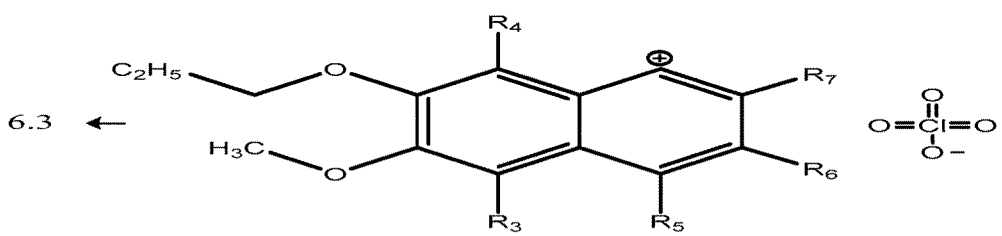
FIG. 30: 6-methoxy-2,3,4,5,8-pentamethyl-7-propoxynaphatehalen-1-ylium
Figure 31:
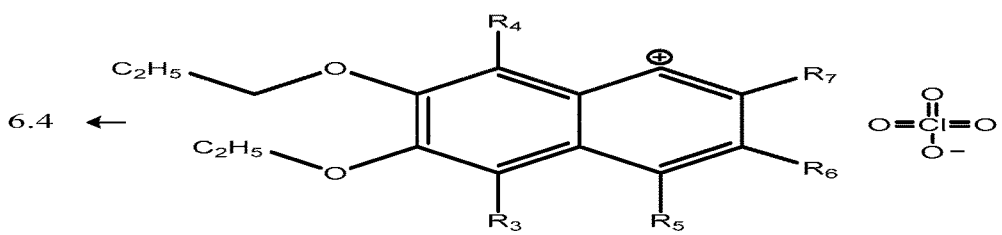
FIG. 31: 6-ethoxy-2,3,4,5,8-pentamethyl-7-propoxynaphatehalen-1-ylium
Figure 32:
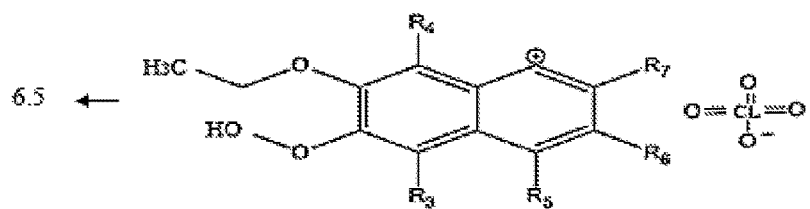
FIG. 32: 7-ethoxy-6-hydroperoxy-2,3,4,5,8-pentamethyl naphatehalen-1-ylium
Figure 33:
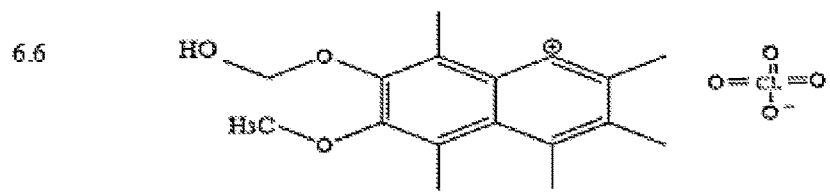
FIG. 33: 7-(hydroxymethoxy)-6-methoxy-2,3,4,5,8-pentamethyl naphatehalen-1-ylium
Figure 34:
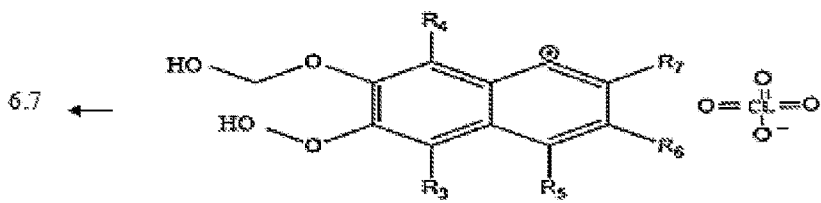
FIG. 34: 6-hydroperoxy-7-(hydroxymethoxy)-2,3,4,5,8-pentamethyl naphatehalen-1-ylium
Figure 35:
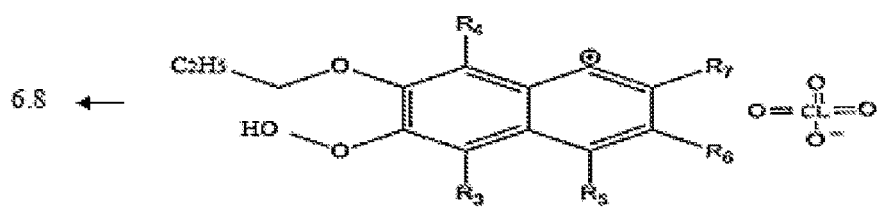
FIG. 35: 6-hydroperoxy-2,3,4,5,8-pentamethyl-7-propoxynaphatehalen-1-ylium
Figure 36:
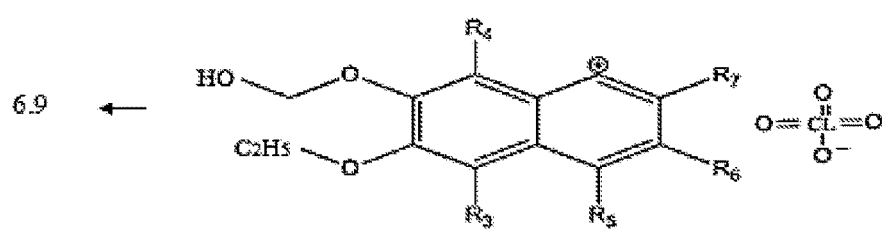
FIG. 36: 6-ethoxy-7-(hydroxymethoxy)-2,3,4,5,8-pentamethylnaphatehalen-1-ylium
Figure 37:
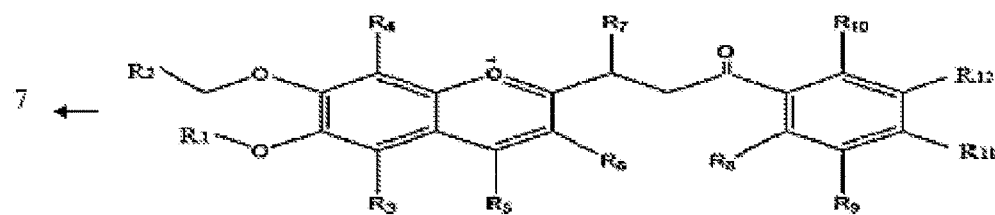
FIG. 37: 4th structure produced from FIG. 5.
Figure 38:
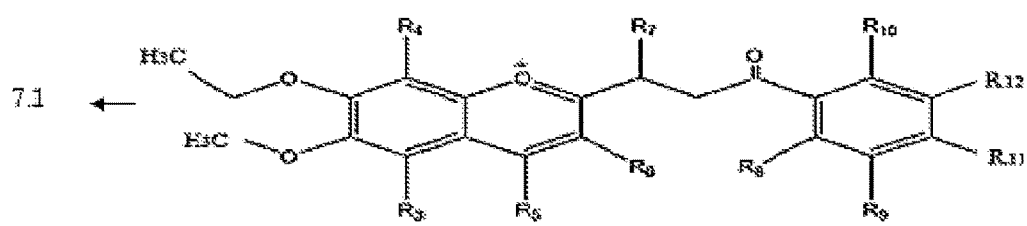
FIG. 38: 2-(4-(3,4-dimethoxy-2,5,6-trimethylphenyl)butan-2-yl)-7-ethoxy-6-methoxy-3,4,5,8-tetramethyl-1$\lambda^3$-chromen and methyl-$\lambda^1$-oxidane (4:1:1) formaldehyde compound
Figure 39:
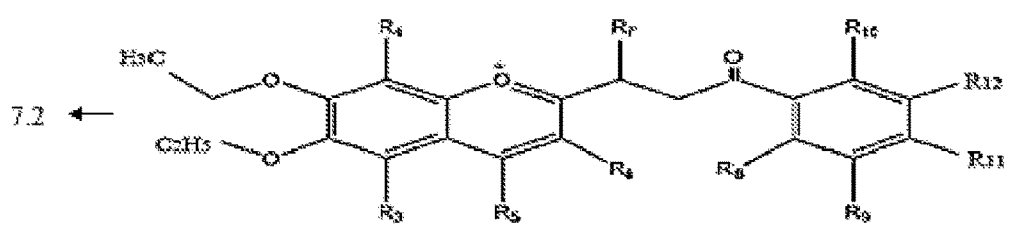
FIG. 39: 2-(4-(3,4-dimethoxy-2,5,6-trimethylphenyl)butan-2-yl)-6,7-diethoxy-3,4,5,8-tetramethyl-1$\lambda^3$-chromen and methyl-$\lambda^1$-oxidane (3:1:1) formaldehyde compound
Figure 40:
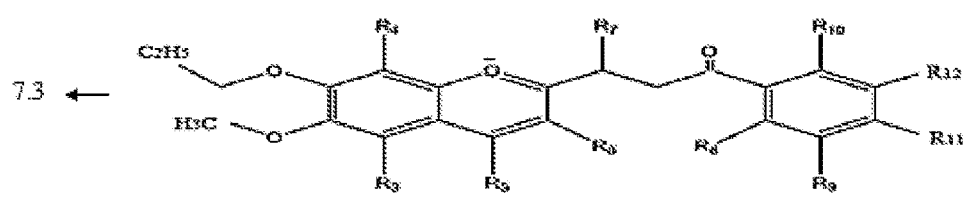
FIG. 40: 2-(4-(3,4-dimethoxy-2,5,6-trimethylphenyl)butan-2-yl)-6-methoxy-3,4,5,8-tetramethyl-7-propoxy-1$\lambda^3$-chromen and methyl-$\lambda^1$-oxidane (3:1:1) formaldehyde compound
Figure 41:
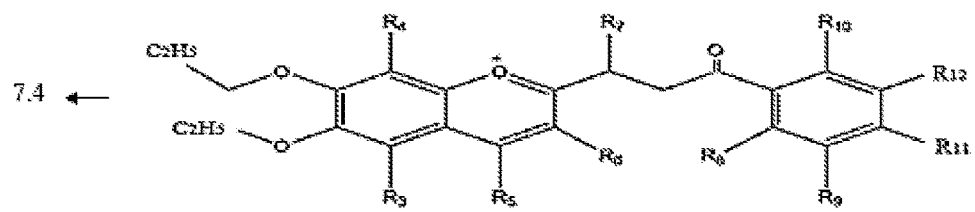
FIG. 41: 2-(4-(3,4-dimethoxy-2,5,6-trimethylphenyl)butan-2-yl)-6-ethoxy-3,4,5,8-tetramethyl-7-propoxy-1$\lambda^3$-chromen and methyl-$\lambda^1$-oxidane (3:1:1) formaldehyde compound
Figure 42:
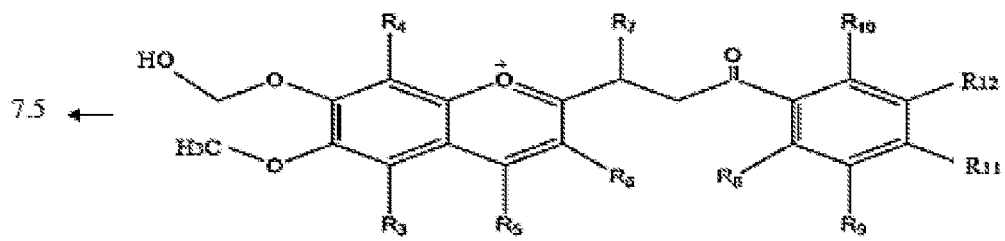
FIG. 42: 2-(4-(3,4-dimethoxy-2,5,6-trimethylphenyl)butan-2-yl)-7-ethoxy-6-hydroperoxy-3,4,5,8-tetramethyl-1$\lambda^3$-chromen and methyl-$\lambda^1$-oxidane (3:1:1) formaldehyde compound
Figure 43:
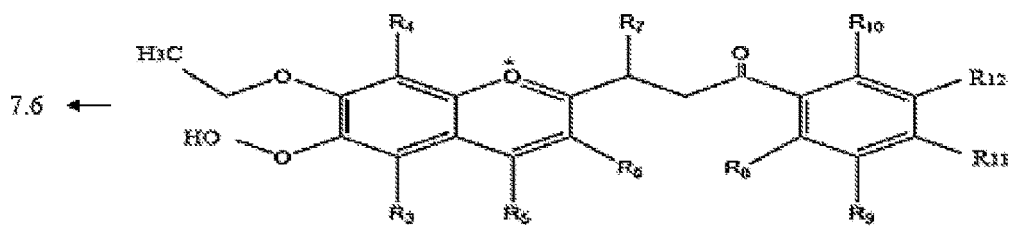
FIG. 43: 2-(4-(3,4-dimethoxy-2,5,6-trimethylphenyl)butan-2-yl)-6-methoxy-3,4,5,8-tetramethyl-1$\lambda^3$-chromen-7-yl)oxy)methanol and methyl-$\lambda^1$-oxidane (3:1:1) formaldehyde compound
Figure 44:
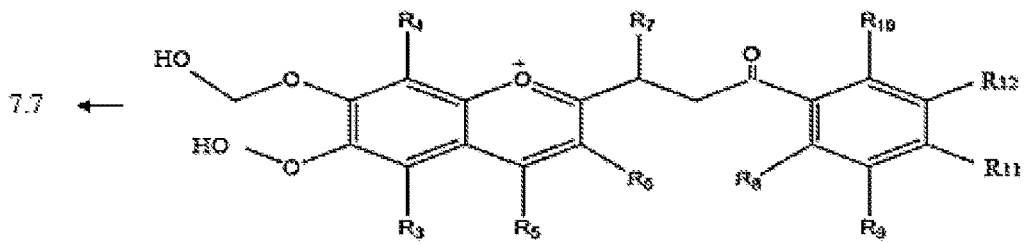
FIG. 44: 2-(4-(3,4-dimethoxy-2,5,6-trimethylphenyl)butan-2-yl)-6-hydroperoxy-3,4,5,8-tetramethyl-1$\lambda^3$-chromen-7-yl)oxy)methanol and methyl-$\lambda^1$-oxidane (3:1:1) formaldehyde compound
Figure 45:
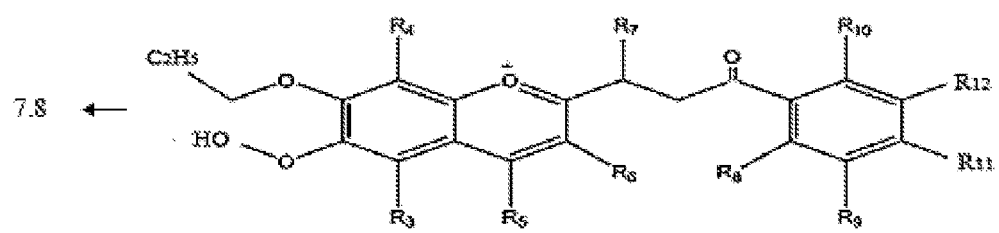
FIG. 45: 2-(4-(3,4-dimethoxy-2,5,6-trimethylphenyl)butan-2-yl)-6-hydroperoxy-3,4,5,8-tetramethyl-7-propoxy-1$\lambda^3$-chromen and methyl $\lambda^1$-oxidane (3:1:1) formaldehyde compound
Figure 46:
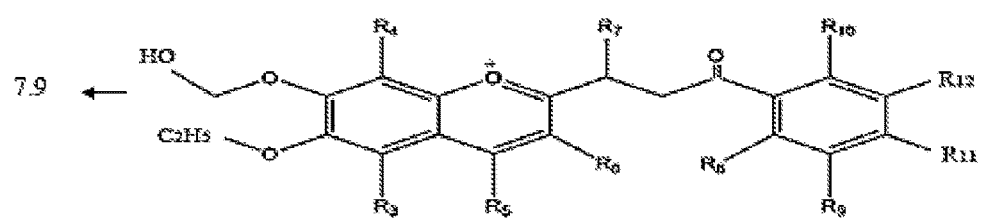
FIG. 46: 2-(4-(3,4-dimethoxy-2,5,6-trimethylphenyl)butan-2-yl)-6-ethoxy-3,4,5,8-tetramethyl-1$\lambda^3$-chromen-7-yl)oxy)methanol and methyl-$\lambda^1$-oxidane (3:1:1) formaldehyde compound
Figure 47:
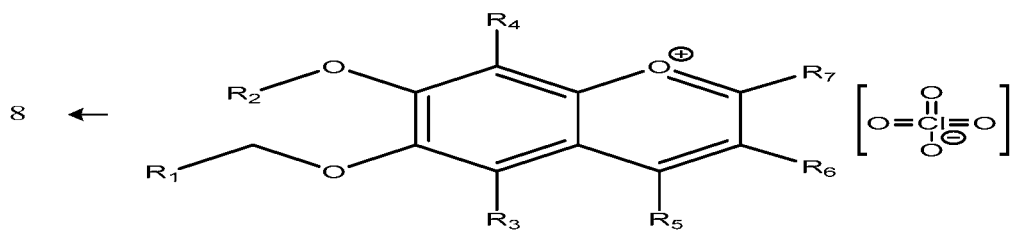
FIG. 47: 5th structure produced from FIG. 5.
Figure 48:
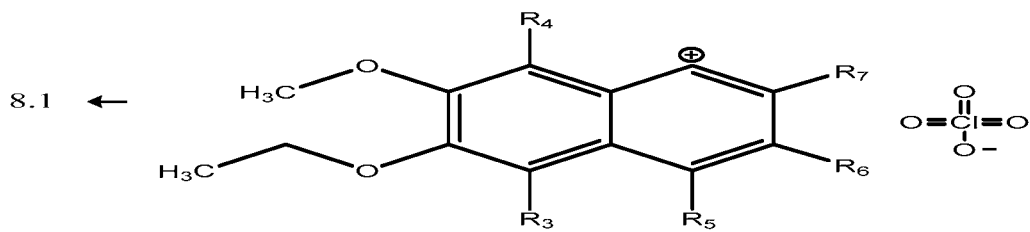
FIG. 48: 6-ethoxy 7-methoxy-2,3,4,5,8-pentamethyl-naphatehalen-1-ylium
Figure 49:
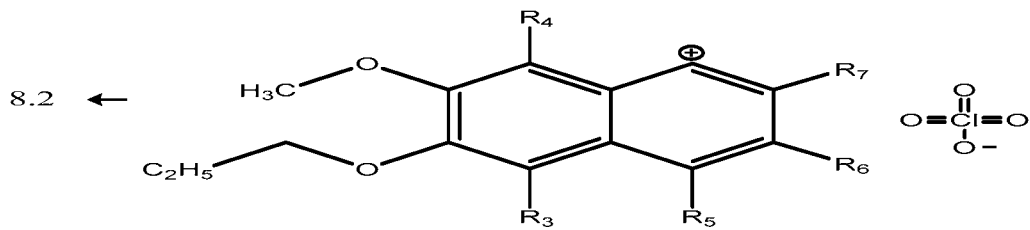
FIG. 49: 7-methoxy-2,3,4,5,8-pentamethyl-6-propoxynaphatehalen-1-ylium
Figure 50:
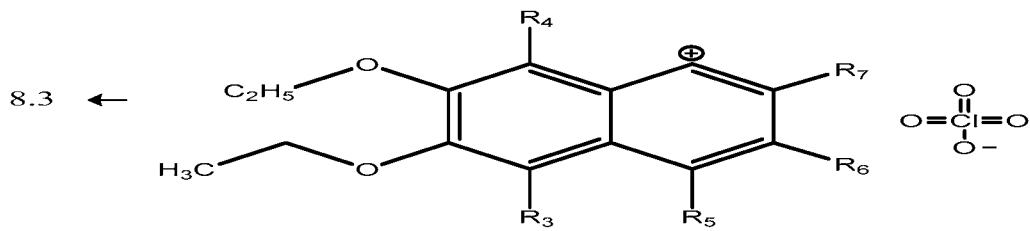
FIG. 50: 6,7-diethoxy-2,3,4,5,8-pentamethylnaphatehalen-1-ylium
Figure 51:
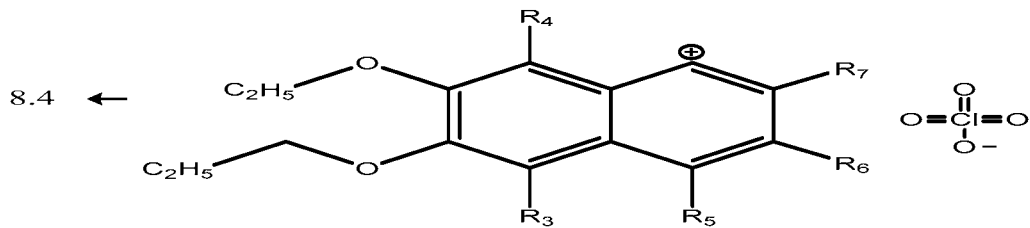
FIG. 51: 7-ethoxy-2,3,4,5,8-pentamethyl-6-propoxynaphatehalen-1-ylium
Figure 52:
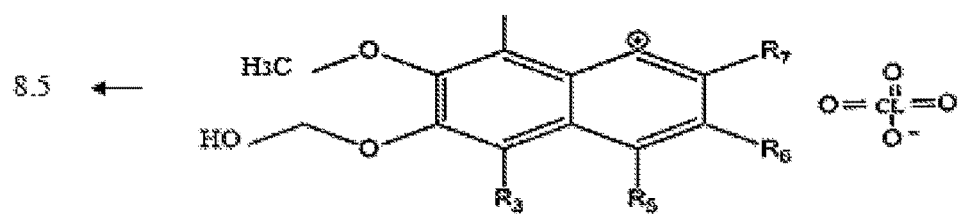
FIG. 52: 6-(hydroxymethoxy)-7-methoxy-2,3,4,5,8-pentamethylnaphatehalen-1-ylium
Figure 53:
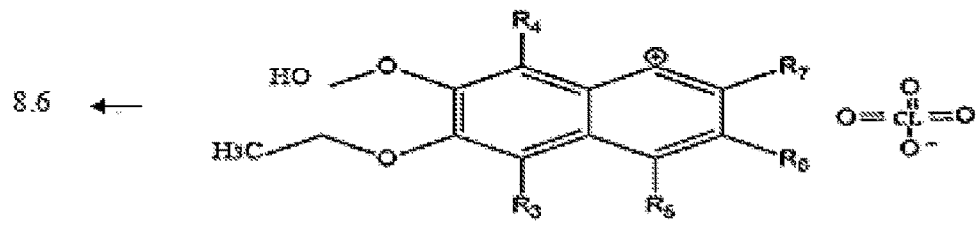
FIG. 53: 6-ethoxy-7-hydroperoxy-2,3,4,5,8-pentamethylnaphatehalen-1-ylium
Figure 54:
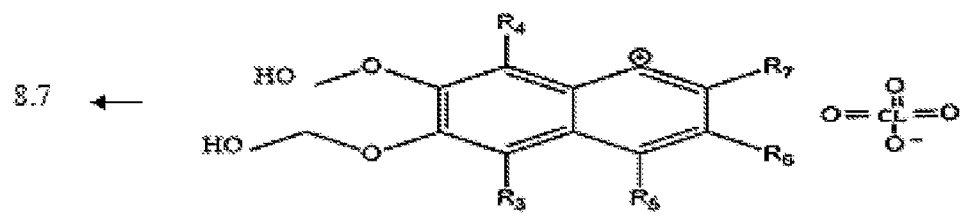
FIG. 54: 7-hydroperoxy-6-(hydroxymethoxy)-2,3,4,5,8-pentamethylnaphatehalen-1-ylium
Figure 55:
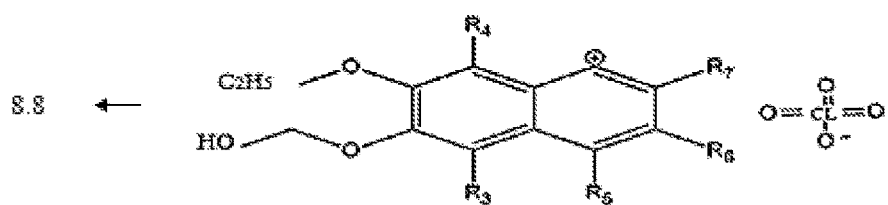
FIG. 55: 7-ethoxy-6-(hydroxymethoxy)-2,3,4,5,8-pentamethylnaphatehalen-1-ylium
Figure 56:
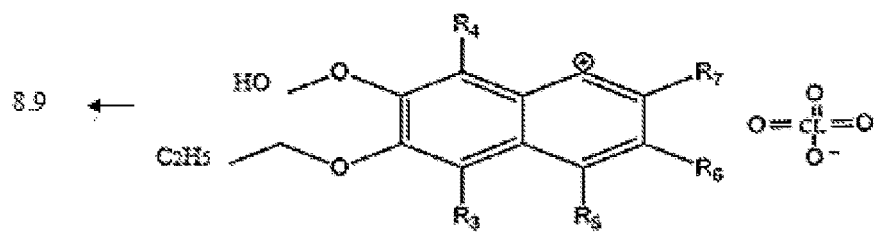
FIG. 56: 7-hydroperoxy-2,3,4,5,8-pentamethyl-6-propoxynaphatehalen-1-ylium
Figure 57:
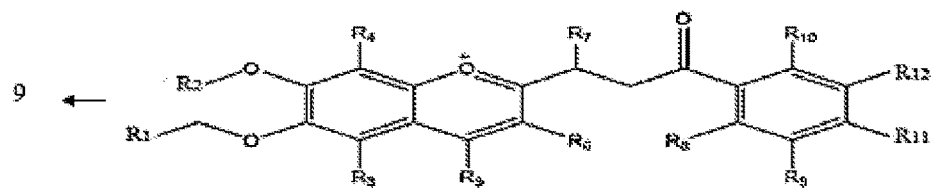
FIG. 57: 6th structure produced from FIG. 5.
Figure 58:
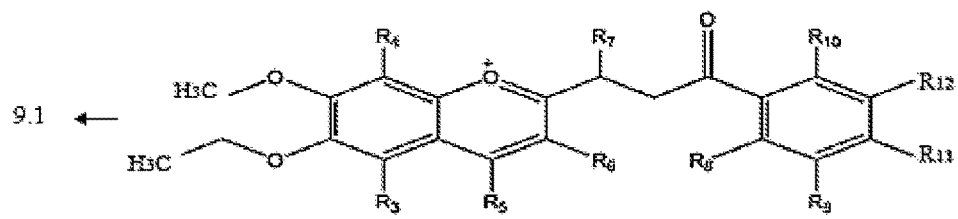
FIG. 58: 1-(3,4-dimethoxy-2,5,6-trimethylphenyl)-3-(6-ethoxy-7-methoxy-3,4,5,8-tetramethyl-1$\lambda^3$-chromen-2-yl)butan-1-one and methyl $\lambda^1$-oxidane (3:1:1) formaldehyde compound
Figure 59:
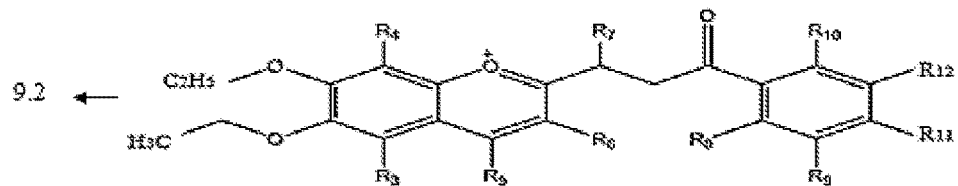
FIG. 59: 3-(6,7-diethoxy-3,4,5,8-tetramethyl-1$\lambda^3$-chromen-2-yl)-1-(3,4-dimethoxy-2,5,6-trimethylphenyl)butan-1-one- and methyl-$\lambda^1$-oxidane (3:1:1) formaldehyde compound
Figure 60:
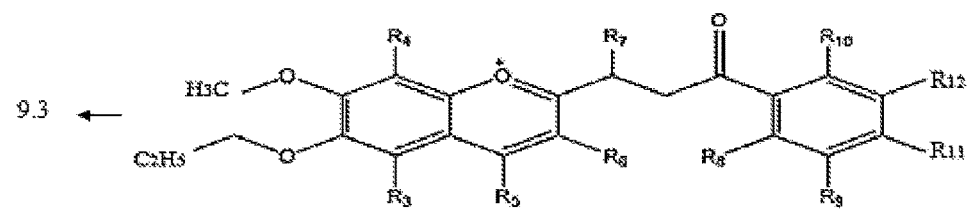
FIG. 60: 1-(3,4-dimethoxy-2,5,6-trimethylphenyl)-3-(7-methoxy-3,4,5,8-tetramethyl-6-propoxy-1$\lambda^3$-chromen-2-yl)butan-1 l-one and methyl $\lambda^1$-oxidane (3:1:1) formaldehyde compound
Figure 61:
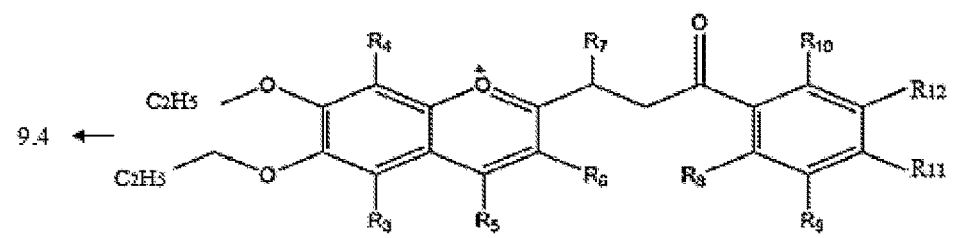
FIG. 61: 1-(3,4-dimethoxy-2,5,6-trimethylphenyl)-3-(7-ethoxy-3,4,5,8-tetramethyl-6-propoxy-1$\lambda^3$-chromen-2-yl)butan-1-one and methyl $\lambda^1$-oxidane (3:1:1) formaldehyde compound
Figure 62:
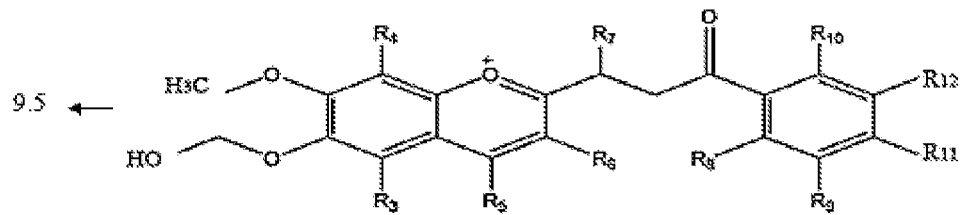
FIG. 62: 1-(3,4-dimethoxy-2,5,6-trimethylphenyl)-3-(6-(hydroxymethoxy)-7-methoxy-3,4,5,8-tetramethyl-1$\lambda^3$-chromen-2-yl)butan-1-one and methyl $\lambda^1$-oxidane (3:1:1) formaldehyde compound
Figure 63:
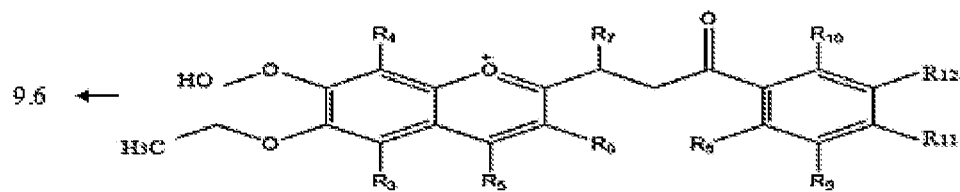
FIG. 63: 1-(3,4-dimethoxy-2,5,6-trimethylphenyl)-3-(6-ethoxy-7-hydroperoxy-3,4,5,8-tetramethyl-1$\lambda^3$-chromen-2-yl)butan-1-one- and methyl-$\lambda^1$-oxidane (3:1:1) formaldehyde compound
Figure 64:
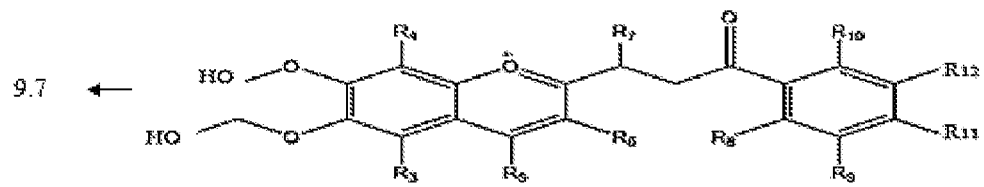
FIG. 64: 1-(3,4-dimethoxy-2,5,6-trimethylphenyl)-3-(7-hydroperoxy-6-(hydroxyperoxy)-3,4,5,8-tetramethyl-1$\lambda^3$-chromen-2-yl)butan-1-one and methyl $\lambda^1$-oxidane (3:1:1) formaldehyde compound
Figure 65:
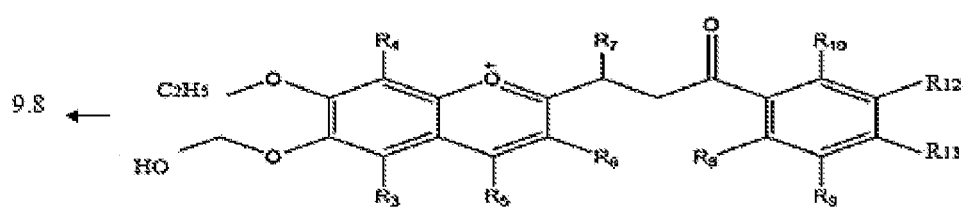
FIG. 65: 1-(3,4-dimethoxy-2,5,6-trimethylphenyl)-3-(7-ethoxy-6-(hydroxyperoxy)-3,4,5,8-tetramethyl-1$\lambda^3$-chromen-2-yl)butan-1-one and methyl $\lambda^1$-oxidane (3:1:1) formaldehyde compound
Figure 66:
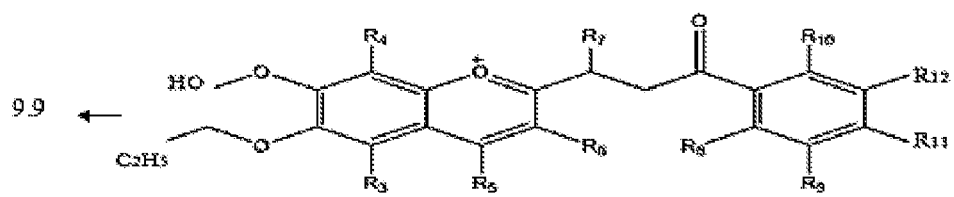
FIG. 66: 1-(3,4-dimethoxy-2,5,6-trimethylphenyl)-3-(7-hydroperoxy-3,4,5,8-tetramethyl-6-propoxy-1$\lambda^3$-chromen-2-yl)butan-1-one and methyl $\lambda^1$-oxidane (3:1:1) formaldehyde compound
Figure 67:
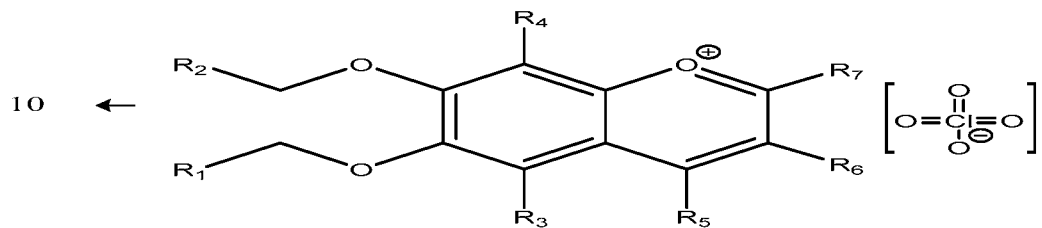
FIG. 67: 7th structure produced from FIG. 5.
Figure 68:
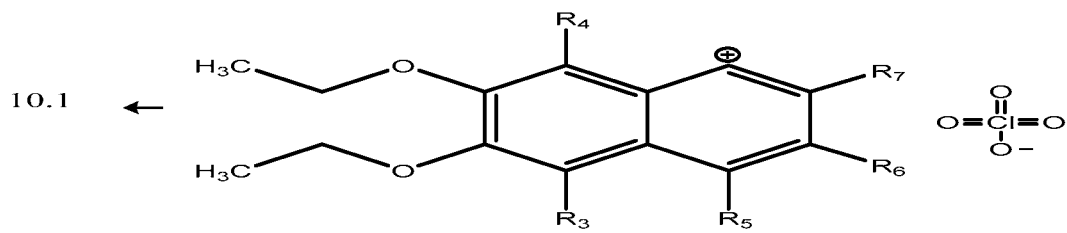
FIG. 68: 6,7-diethoxy-2,3,4,5,8-pentamethylnaphatehalen-1-ylium
Figure 69:
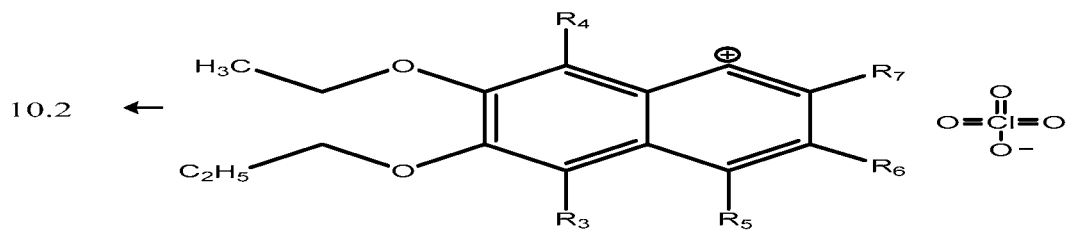
FIG. 69: 7-ethoxy-2,3,4,5,8-pentamethyl-6-propoxynaphatehalen-1-ylium
Figure 70:
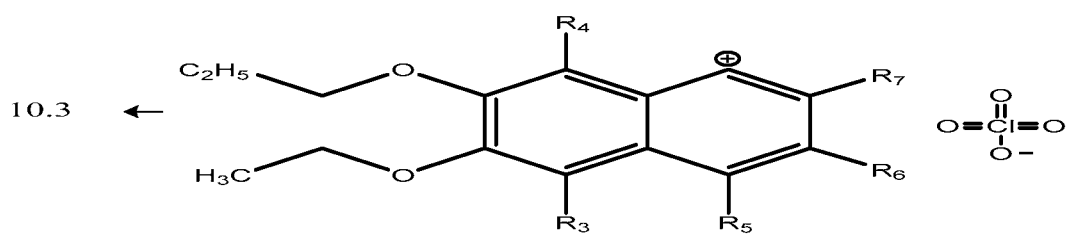
FIG. 70: 6-ethoxy-2,3,4,5,8-pentamethyl-7-propoxynaphatehalen-1-ylium
Figure 71:
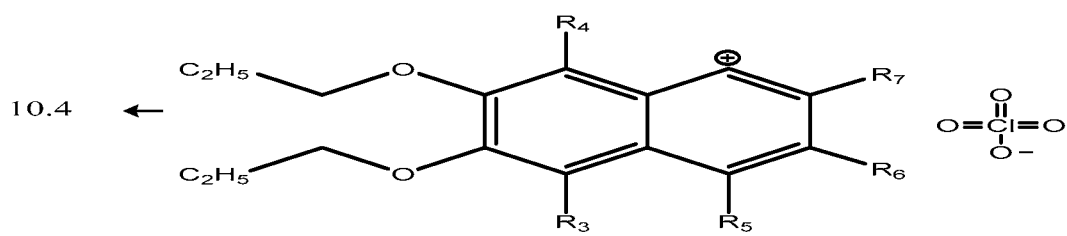
FIG. 71: 2,3,4,5,8-pentamethyl-6,7-dipropoxynaphatehalen-1-ylium
Figure 72:
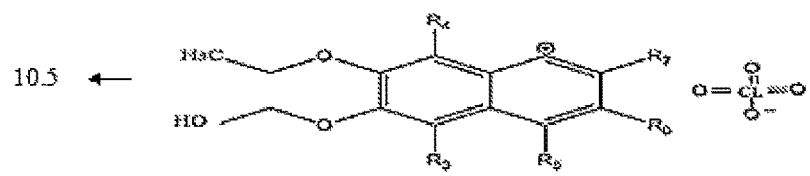
FIG. 72: 7-ethoxy-6-(hydroxymethoxy)-2,3,4,5,8-pentamethylnaphatehalen-1-ylium
Figure 73:
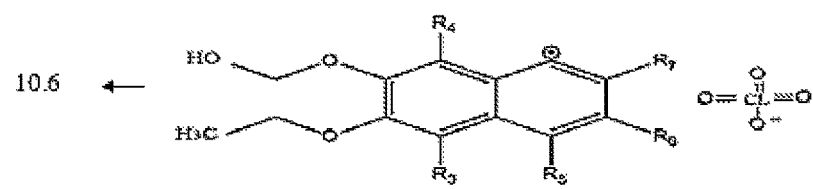
FIG. 73: 6-ethoxy-7-(hydroxymethoxy)-2,3,4,5,8-pentamethylnaphatehalen-1-ylium
Figure 74:
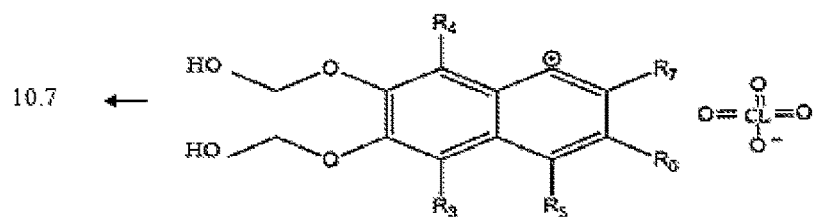
FIG. 74: 6,7-bis(hydroxymethoxy)-2,3,4,5,8-pentamethynaphatehalen-1-ylium
Figure 75:
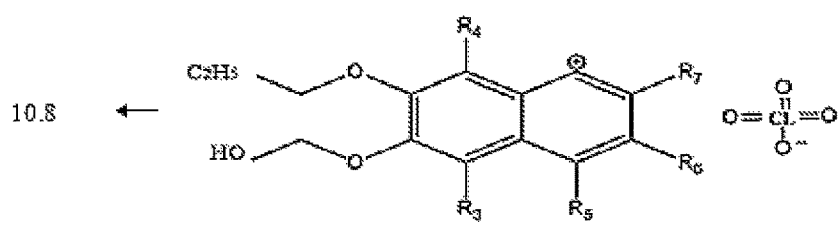
FIG. 75: 6-(hydroxymethoxy)-2,3,4,5,8-pentamethyl-7-propoxynaphatehalen-1-ylium
Figure 76:
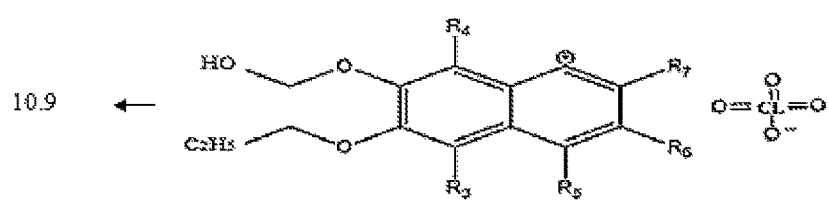
FIG. 76: 7-(hydroxymethoxy)-2,3,4,5,8-pentamethyl-6-propoxynaphatehalen-1-ylium
Figure 77:
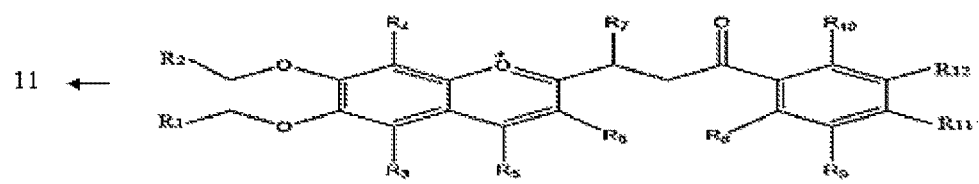
FIG. 77: 8th structure produced from FIG. 5.
Figure 78:
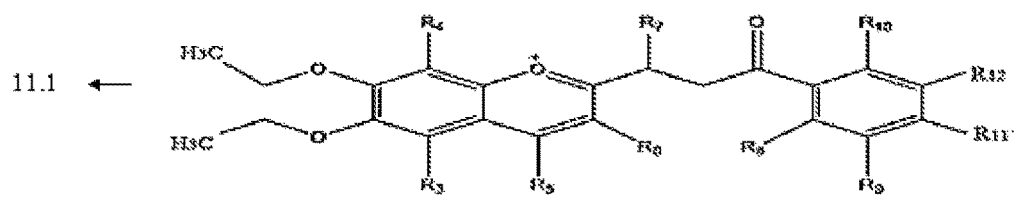
FIG. 78: 3-(6,7-diethoxy-3,4,5,8-tetramethyl-1$\lambda^3$-chromen-2-yl)-1-(3,4-dimethoxy-2,5,6-trimethylphenyl)butan-1-one- and methyl-$\lambda^1$-oxidane (3:1:1) formaldehyde compound
Figure 79:
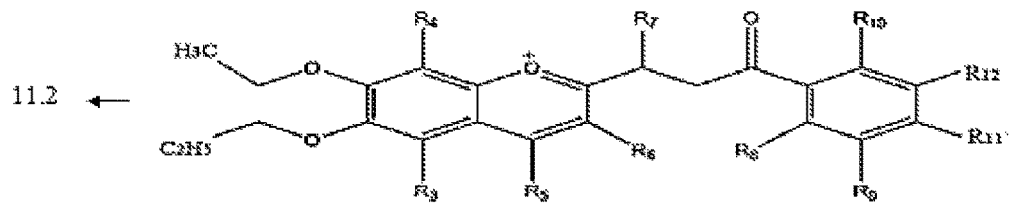
FIG. 79: 1-(3,4-dimethoxy-2,5,6-trimethylphenyl)-3-(7-ethoxy,3,4,5,8-tetramethyl-6-propoxy-1$\lambda^3$-chromen-2-yl)butan-1-one-methyl-$\lambda^1$-oxidane (3:1:1) formaldehyde compound
Figure 80:
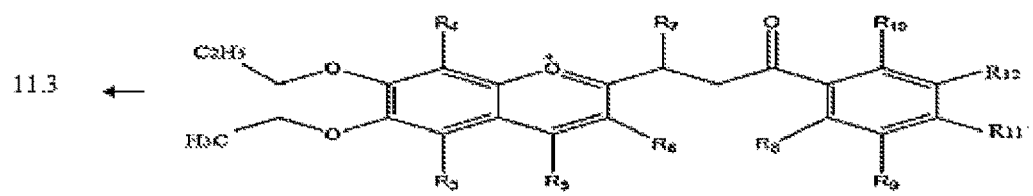
FIG. 80: 1-(3,4-dimethoxy-2,5,6-trimethylphenyl)-3-(6-ethoxy-3,4,5,8-tetramethyl-7-propoxy-1$\lambda^3$-chromen-2-yl)butan-1-one-methyl-$\lambda^1$-oxidane (3:1:1) formaldehyde compound
Figure 81:
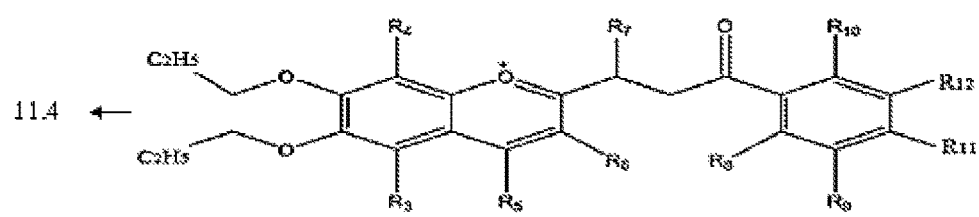
FIG. 81: 1-(3,4-dimethoxy-2,5,6-trimethylphenyl)-3-(3,4,5,8-tetramethyl-6,7-dipropoxy-1$\lambda^3$-chromen-2-yl)butan-1-one-methyl-$\lambda^1$-oxidane (3:1:1) formaldehyde compound
Figure 82:
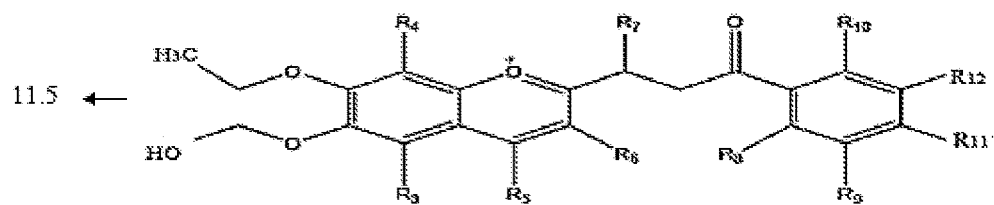
FIG. 82: 1-(3,4-dimethoxy-2,5,6-trimethylphenyl)-3-(7-ethoxy-6-(hydroxyperoxy)-3,4,5,8-tetramethyl-1$\lambda^3$-chromen-2-yl)butan-1-one and methyl $\lambda^1$-oxidane (3:1:1) formaldehyde compound
Figure 83:
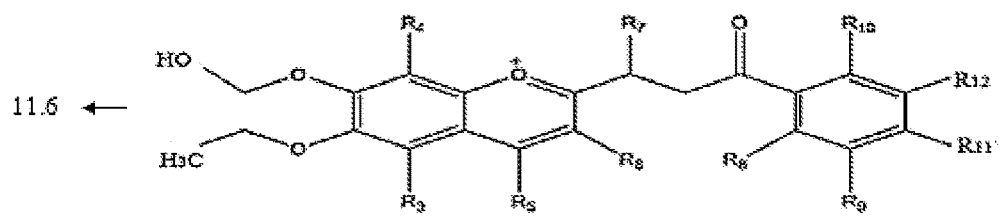
FIG. 83: 1-(3,4-dimethoxy-2,5,6-trimethylphenyl)-3-(6-ethoxy-7-(hydroxymethoxy)-3,4,5,8-tetramethyl-1$\lambda^3$-chromen-2-yl)butan-1-one-and-methyl-$\lambda^1$-oxidane (3:1:1) formaldehyde compound
Figure 84:
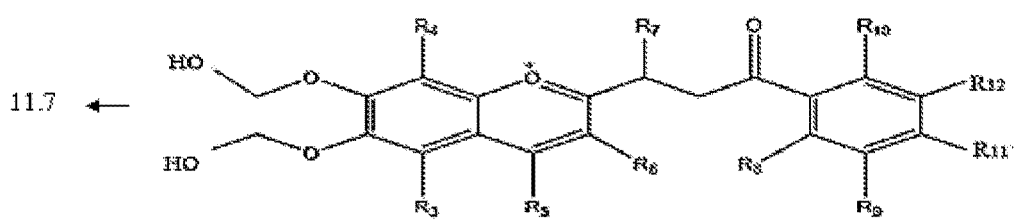
FIG. 84: 3-(6,7-bis(hydroxymethoxy)-3,4,5,8-tetramethyl-1$\lambda^3$-chromen-2-yl)-1-(3,4-dimethoxy-2,5,6-trimethylphenyl)butan-1-one-and-methyl-$\lambda^1$-oxidane (3:1:1) formaldehyde compound
Figure 85:
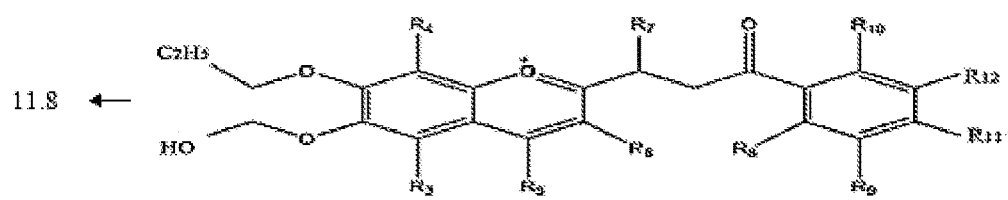
FIG. 85: 1-(3,4-dimethoxy-2,5,6-trimethylphenyl)-3-(6-(hydroxymethoxy)-(3,4,5,8-tetramethyl-7-propoxy-1$\lambda^3$-chromen-2-yl)butan-1-one-and-methyl-$\lambda^1$-oxidane (3:1:1) formaldehyde compound FIG. 86: 1-(3,4-dimethoxy-2,5,6-trimethylphenyl)-3-(7-(hydroxymethoxy)-(3,4,5,8-tetramethyl-6-propoxy-1$\lambda^3$-chromen-2-yl)butan-1-one-and-methyl-$\lambda^1$-oxidane (3:1:1) formaldehyde compound.
Figure 86:
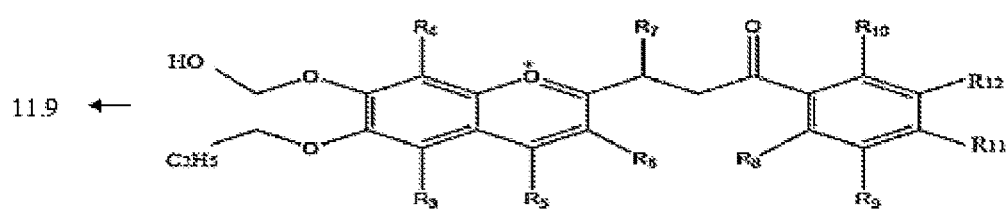

10.1: 6,7-diethoxy-2,3,4,5,8-pentamethylnaphatehalen-1-ylium 10.2: 7-ethoxy-2,3,4,5,8-pentamethyl-6-propoxynaphatehalen-1-ylium 10.3: 6-ethoxy-2,3,4,5,8-pentamethyl-7-propoxynaphatehalen-1-ylium 10.4: 2,3,4,5,8-pentamethyl-6,7-dipropoxynaphatehalen-1-ylium 10.3: 7-ethoxy-6-(hydroxymethoxy)-2,3,4,5,8-pentamethylnaphatehalen-1-ylium 10.6: 6-ethoxy-7-(hydroxymethoxy)-2,3,4,5,8-pentamethylnaphatehalen-1-ylium 10.7: 6,7-bis(hydroxymethoxy)-2,3,4,5,8-pentamethylnaphatehalen-1-ylium 10.8: 6-(hydroxymethoxy)-2,3,4,5,8-pentamethyl-7-propoxynaphatehalen-1-ylium 10.9: 7-(hydroxymethoxy)-2,3,4,5,8-pentamethyl-6-propoxynaphatehalen-1-ylium 11: 8th structure produced from FIG. 5 11.1: 3-(6,7-diethoxy-3,4,5,8-tetramethyl-1λ³-chromen-2-yl)-1-(3,4-dimethoxy-2,5,6-trimethylphenyl)butan-1-one and methyl-λ¹-oxidane (3:1:1) formaldehyde compound 11.2: 1-(3,4-dimethoxy-2,5,6-trimethylphenyl)-3-(7-ethoxy,3,4,5,8-tetramethyl-6-propoxy-1λ³-chromen-2-yl)butan-1-one-methyl-λ¹-oxidane (3:1:1) formaldehyde compound 11.3: 1-(3,4-dimethoxy-2,5,6-trimethylphenyl)-3-(6-ethoxy-3,4,5,8-tetramethyl-7-propoxy-1λ³-chromen-2-yl)butan-1-one-methyl-λ¹-oxidane (3:1:1) formaldehyde compound 11.4: 1-(3,4-dimethoxy-2,5,6-trimethylphenyl)-3-(0,3,4,5,8-tetramethyl-6,7-dipropoxy-1λ³-chromen-2-yl)butan-1-one-methyl-λ¹-oxidane (3:1:1) formaldehyde compound 11.5: 1-(3,4-dimethoxy-2,5,6-trimethylphenyl)-3-(7-ethoxy-6-(hydroxyperoxy)-3,4,5,8-tetramethyl-1λ³-chromen-2-yl)butan-1-one and methyl λ¹-oxidane (3:1:1) formaldehyde compound 11.6: 1-(3,4-dimethoxy-2,5,6-trimethylphenyl)-3-(6-ethoxy-7-(hydroxymethoxy)-3,4,5,8-tetramethyl-1λ³-chromen-2-yl)butan-1-one-and-methyl-λ¹-oxidane (3:1:1) formaldehyde compound 11.7: 3-(6,7-bis(hydroxymethoxy)-3,4,5,8-tetramethyl-1λ³-chromen-2-yl)-1-(3,4-dimethoxy-2,5,6-trimethylphenyl)butan-1-one-and-methyl-λ¹-oxidane (3:1:1) formaldehyde compound 11.8: 1-(3,4-dimethoxy-2,5,6-trimethylphenyl)-3-(6-(hydroxymethoxy)-(3,4,5,8-tetramethyl-7-propoxy-1λ³-chromen-2-yl)butan-1-one-and-methyl-λ¹-oxidane (3:1:1) formaldehyde compound 11.9: 1-(3,4-dimethoxy-2,5,6-trimethylphenyl)-3-(7-(hydroxymethoxy)-(3,4,5,8-tetramethyl-6-propoxy-1λ³-chromen-2-yl)butan-1-one-and-methyl-λ¹-oxidane (3:1:1) formaldehyde compound

DESCRIPTION OF THE INVENTION

Figure 1:
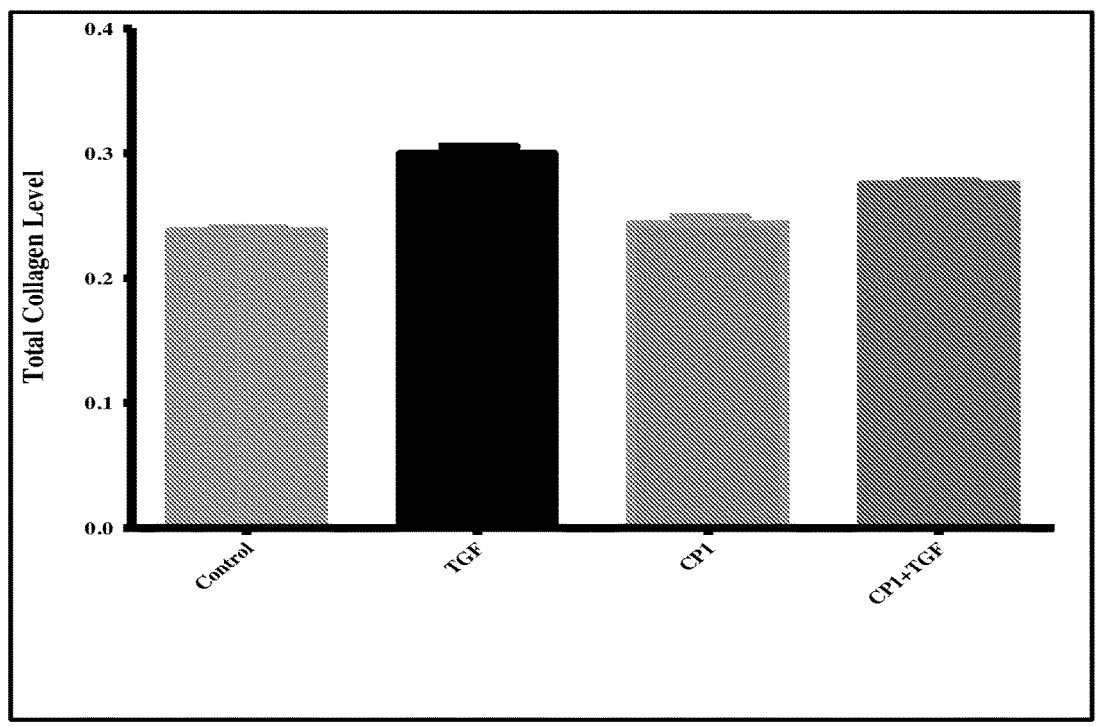
FIG. 1: Inhibitor effect of 6,7-dimethoxy 2H-chromen-one (1) on TGFbeta-induced collagen synthesis in L929 cells.
Figure 2:
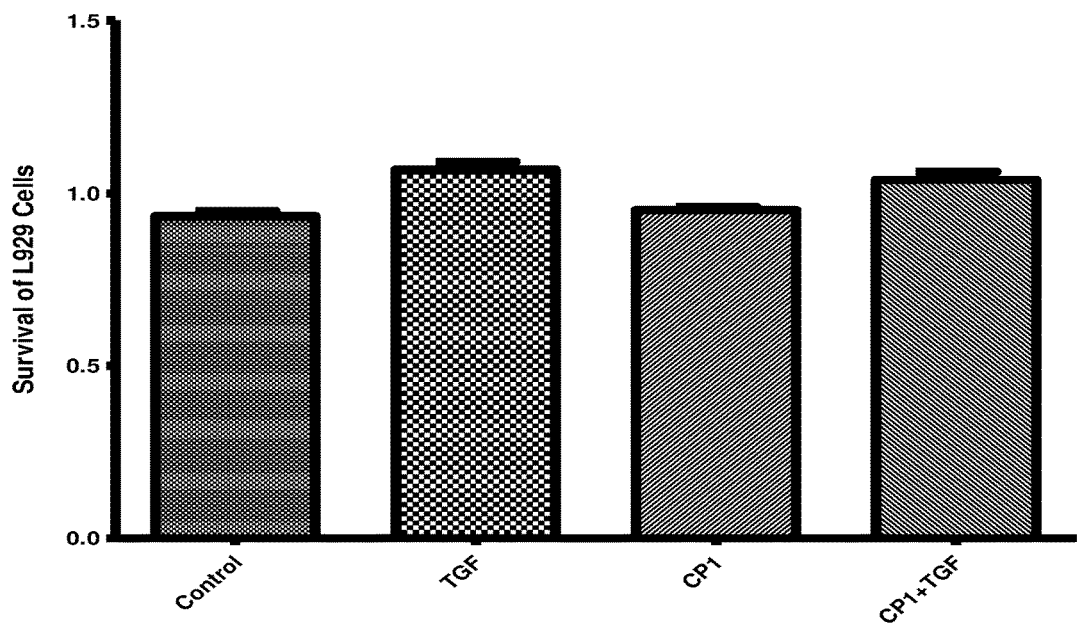
FIG. 2: Inhibitor effect of 6,7-dimethoxy 2H-chromen-one (1) on proliferation of L929 cells.
Figure 3:
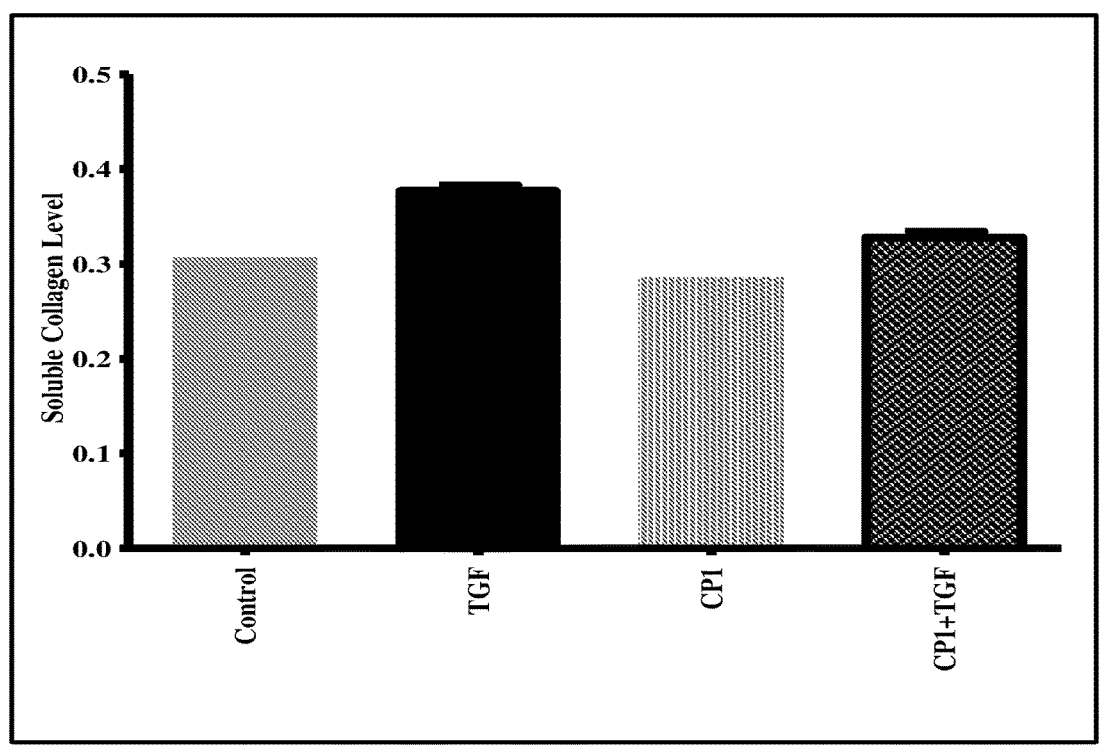
FIG. 3: Inhibitor effect of 6,7-dimethoxy 2H-chromen-one (1) on TGFbeta-induced secreted collagen synthesis in L929 cells

The present invention is about novel compounds which may offer alternative treatment options against IPF, which believed to develop as a consequences of smoking, pollution, allergens, toxins and seen in people who are older than 50 years old. The compounds mentioned in this application have been generated from "6,7-dimethoxy 2H-chromen-one (1), which was identified from local medicinal plants during our screening studies. The anti-fibrotic activity of this compound ("6,7-dimethoxy 2H-chromen-one (I) against TGF beta-induced collagen synthesis using 1.929 cells has been identified. For this, in 96-well plates, 1.929 cells were cultured in DMEM supplemented with % 10 serum, 10 μg/ml ascorbic acid and 20 μM prolin until they reached to confluency. Confluent cells were treated with 50 micromole of our compound (named as CP1) dissolved in DMSO for 1 hour, then 5 ng/ml of Mouse TGFβ2 was added and cells were further incubated for 72 hours at incubator supplied with 5% $CO_2$ and 80% humidity. At the end of this incubation one of the plate was used to determine cell viability by using MTT test, FIG. 2. The second 96-well plate was used to determine the level of total collagen. To determine the level of total collagen medium was removed and cells were fixed to bottom of the plated by adding % 0.5 gluteraldehyde prepared in 1×PBS for 30 minutes, then gluteraldehyde was removed, cells were washed with water and incubated with 100 microliter of 0.5 molar acetic acid for 30 minutes. At the end of 30 min, acetic acid was removed, cells were washed with water, air dried and 100 microliter "sircol dye solution" was added and further incubated for two hours at room temperature. Then, "sircol dye solution" was removed, plates was washed with water, air dried and 300 microliter of alkaline solution was added and shaken for 3 hours at room temperature to extract collagen-bound sircol. Absorbance of developed color was determined at 600 nm. As shown at FIG. 1, TGFβ induced collagen level by % 20 compared to control cells, however, in the presence of CP1 TGFβ induced collagen level by % 10, in other words CP1 inhibited TGFβ-induced collagen synthesis by % 50. In addition to total collagen, we also determined the level of "secreted collagen" by using ELISA. Briefly, supernatant (200 microliter) of cultured cells were transferred into "high affinity binding ELISA plates" and incubated this at 4° C. for 16 hours, then supernatant was removed, plate was washed with PBST (% 0.1 Tween-20 in 1×PBS) and blocked with % 1 BSA prepared in PBST for 2 hours, plate was washed with PBST and anti-collagen type I antibody (1:2000 dilution) prepared in % 1 BSA was added and incubated for 1 hour at room temperature, this antibody was removed, plate was washed with PBST and relevant secondary antibody prepared in % 1 BSA was added at 1:2000 dilution and incubated at room temperature for 1 hour, then secondary antibody was removed, plate was washed with PBST and ELISA was performed. As shown at FIG. 3, present compound (CP1) significantly inhibits TGFβ-induced secreted collagen level. These results strongly indicate that the compounds derived from CP1 may offer alternative treatment options to treat fibrosis patients.

Structure of the above mentioned (CP1) compound is 6,7-dimethoxy 2H-chromen-2-one (1) and its chemical Formula is $C_{11}H_{10}O_4$

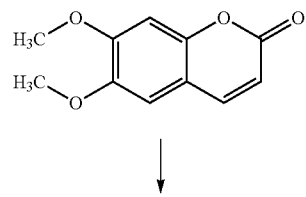

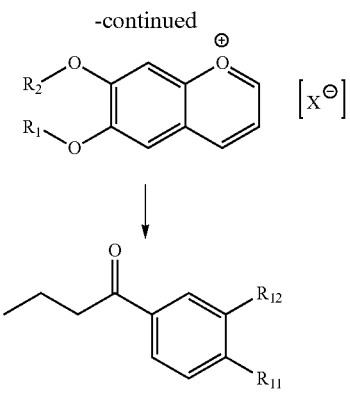

With this application, carbonyl oxygen is removed from Chromene structure, this yielded positively charged chromene ring, then from this structure, 8 different molecules (4,5,6,7,8,9,10,11) and their 9 different combinations were generated.

R1 and R2 positions of these 8 compound were chosen as site of modifications, and methyl(—CH3), ethyl(—C2H5), hydroxyl (—OH), and their combinations with one another were chosen to represent R and R2.

Eight different structure and their derivatives are explained below;

In the first compound (4), produced from main compound (2): when R1 and R2 are methyl (—CH3), and in this compound (6,7-dimethoxy-chromenylium perchlorate (4.1) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the first compound (4), produced from main compound (2); when R1 is ethyl (—C2H5) and R2 is methyl(—CH3), and in this compound (6-ethoxy-7 methoxy 2,3,4,5,8-pentamethyl naphatehalen-1-ylium (4.2); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the first compound (4), produced from main compound (2); when R1 is methyl (—CH3) and R2 is ethyl(—C2H5), and in this compound (7-ethoxy-6-methoxy-2,3,4,5,8-pentamethyl naphatehalen-1-ylium (4.3) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the first compound (4), produced from main compound (2); when R1 and R2 are ethyl(—C2H5), and in this compound (6,7-diethoxy-2,3,4,5,8-pentamethyl naphatehalen-1-ylium) (4.4); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_1$-$C_6$ alkenyl, carboxyl (—COOH) and their combinations with one another.

In the first compound (4), produced from main compound (2): when R1 is hydroxyl (—OH) and R2 is methyl (—CH3), and in this compound (6-hydroperoxy-7-methoxy-2,3,4,5,8-pentamethylnaphatehalen-1-ylium) (4.5); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the first compound (4), produced from main compound (2); when R1 is methyl (—CH3) and R2 is hydroxyl (—OH), and in this compound (7-hydroperoxy-6-methoxy-2,3,4,5,8-pentamethylnaphatehalen-1-ylium) (4.6); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the first compound (4), produced from main compound (2); when R1 and R2 are hydroxyl (—OH), and in this compound (6,7-dihydroperoxy-2,3,4,5,8-pentamethylnaphatehalen-1-ylium) (4.7); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the first compound (4), produced from main compound (2); when R1 is hydroxyl (—OH) and R2 is ethyl (—C2H5, and in this compound (7-ethoxy-6-hydroperoxy-2,3,4,5,8-pentamethylnaphatehalen-1-ylium) (4.8); R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another In the first compound (4), produced from main compound (2); when R1 is ethyl (—C2H5) and R2 is hydroxyl (—OH), and in this compound (6-ethoxy-7-hydroperoxy-2,3,4,5,8-pentamethyl naphatehalen-1-ylium) (4.9) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another In the second compound (5), produced from main compound (2); when R1, R2, R11 and R12 are methyl (—CH3), and in this compound (2-(4-(3,4-dimethoxy-2,5,6-trimethylphenyl)butan-2-yl)-6,7-dimethoxy-3,4,5,8-tetramethyl-1$\lambda^3$-chromen-(1:1) formaldehyde compound (5.1) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 is ethyl (—C2H5) R2 is methyl (—CH3), R11 and R12 are methyl —CH3 and in this compound (2-(4-(3,4-dimethoxy-2,5,6-trimethylphenyl)butan-2-yl)-6-ethoxy-7-methoxy-3,4,5,8-tetramethyl-1$\lambda^3$- chromen-(1:1) formaldehyde compound) (5.2) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 is methyl (—CH3), R2 is ethyl (—C2H5), R11 and R12 are methyl (—CH3) and in this compound (2-(4-(3,4-dimethoxy-2,5,6-trimethylphenyl)butan-2-yl)-7-ethoxy-6-methoxy-3,4,5,8-tetramethyl-1$\lambda^3$-chromen-(1:1) formaldehyde compound) (5.2) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 and R2 are ethyl (—C2H5), R11 and R12 are methyl (—CH3) and in this compound (2-(4-(3,4-dimethoxy-2,5,6-trimethylphenyl)butan-2-yl)-6,7-diethoxy-3,4,5,8-tetramethyl-1$\lambda^3$-chromen-(1:1) formaldehyde compound) (5.4) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 is hydroxyl(—OH) R2 is methyl (—CH3), R11 methyl (—CH3), R12 methyl (—CH3) and in this compound (2-(4-(3,4-dimethoxy-2,5,6-trimethylphenyl)butan-2-yl)-6-hydroperoxy-7-methoxy-3,4,5,8-tetramethyl-1$\lambda^3$-chromen (1:1) formaldehyde compound) (5.5) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2): when R1, methyl (—CH3) R2 hydroxyl (—OH), R11 methyl (—CH3), R12 methyl (—CH3) and in this compound (2-(4-(3,4-dimethoxy-2,5,6-trimethylphenyl)butan-2-yl)-6-hydroperoxy-7-methoxy-3,4,5,8-tetramethyl-1$\lambda^3$-chromen (1:1) formaldehyde compound) (5.6) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_1$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 and R2 are hydroxyl (—OH), R11 methyl (—CH3), R12 methyl (—CH3) and in this compound (2-(4-(3,4-dimethoxy-2,5,6-trimethylphenyl)butan-2-yl)-6,7-dihydroperoxy-3,4,5,8-tetramethyl-1$\lambda^3$-chromen (1:1) formaldehyde compound) (5.7) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 is hydroxyl(—OH) and R2 is ethyl (—C2H5), R11 methyl (—CH3), R12 methyl (—CH3), and in this compound (2-(4-(3,4-dimethoxy-2,5,6-trimethylphenyl)butan-2-yl)-7-ethoxy-6-hydroperoxy-3,4,5,8-tetramethyl-1$\lambda^3$-chromen (1:1) formaldehyde compound) (5.8) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the second compound (5), produced from main compound (2); when R1 is ethyl (—C2H5), R2 is hydroxyl (—OH), R11 methyl (—CH3), R12 methyl (—CH3), and in this compound (2-(4-(3,4-dimethoxy-2,5,6-trimethylphenyl)butan-2-yl)-6-ethoxy-7-hydroperoxy-3,4,5,8-tetramethyl-1$\lambda^3$-chromen (1:1) formaldehyde compound) (5.9) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_1$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the third compound (6), produced from main compound (2); when R1 and R2 are methyl (—CH3), and in this compound (7-ethoxy-6-methoxy-2,3,4,5,8-pentamethyl naphatehalen-1-ylium (6.1) R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the third compound (6), produced from main compound (2); when R1 is ethyl (—C2H5) and R2 is methyl (—CH3), and in this compound (6,7-diethoxy-2,3,4,5,8-pentamethyl naphatehalen-1-ylium (6.2) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the third compound (6), produced from main compound (2); when R1 is methyl (—CH3) and R2 is ethyl (—C2H5), and in this compound (6-methoxy-2,3,4,5,8-pentamethyl-7-propoxynaphatehalen-1-ylium (6.3) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the third compound (6), produced from main compound (2); when R1 is ethyl (—C2H5) and R2 is ethyl (—C2H5), and in this compound (6-ethoxy-2,3,4,5,8-pentamethyl-7-propoxynaphatehalen-1-ylium (6.4) R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the third compound (6), produced from main compound (2); when R1 is hydroxyl(—OH) and R2 is methyl (—CH3), and in this compound (7-ethoxy-6-hydroperoxy-2,3,4,5,8-pentamethyl naphatehalen-1-ylium (6.5) R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$alkenyl, carboxyl (—COOH) and their combinations with one another In the third compound (6), produced from main compound (2); when R1 is methyl (—CH3) and R2 is hydroxyl (—OH), and in this compound (7-(hydroxymethoxy)-6-methoxy-2,3,4,5,8-pentamethyl naphatehalen-1-ylium (6.6); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$alkenyl, carboxyl (—COOH) and their combinations with one another.

In the third compound (6), produced from main compound (2); when R1 and R2 are hydroxyl (—OH), and in this compound (6-hydroperoxy-7-(hydroxymethoxy)-2,3,4,5,8-pentamethyl naphatehalen-1-ylium (6.7); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the third compound (6), produced from main compound (2); when R1 is hydroxyl (—OH) and R2 is ethyl (—C2H5), and in this compound (6-hydroperoxy-2,3,4,5,8-pentamethyl-7-propoxynaphatehalen-1-ylium (6.8) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$alkenyl, carboxyl (—COOH) and their combinations with one another.

In the third compound (6), produced from main compound (2); when R1 is ethyl (—C2H5) and R2 is hydroxyl (—OH), and in this compound (6-ethoxy-7-(hydroxymethoxy)-2,3,4,5,8-pentamethylnaphatehalen-1-ylium (6.9); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fourth compound (7), produced from main compound (2); when R1, R2, R1 and R12 are methyl (—CH3), and in this compound (2-(4-(3,4-dimethoxy-2,5,6-trimethylphenyl)butan-2-yl)-7-ethoxy-6-methoxy-3,4,5,8-tetramethyl-1$\lambda^3$-chromen and methyl-$\lambda^1$-oxidane (4:1:1) formaldehyde compound) (7.1); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fourth compound (7), produced from main compound (2); when R1 is ethyl (—C2H5), R2 is methyl (—CH3), R11 and R12 are methyl (—CH3), and in this compound (2-(4-(3,4-dimethoxy-2,5,6-trimethylphenyl)butan-2-yl)-6,7-diethoxy-3,4,5,8-tetramethyl-1$\lambda^3$-chromen and methyl-$\lambda^1$-oxidane (3:1:1) formaldehyde compound) (7.2) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fourth compound (7), produced from main compound (2); when R1 is methyl (—CH3), R2 is ethyl (—C2H5), R11 and R12 are methyl (—CH3), and in this compound (2-(4-(3,4-dimethoxy-2,5,6-trimethylphenyl)butan-2-yl)-6-methoxy-3,4,5,8-tetramethyl-7-propoxy-1$\lambda^3$-chromen and methyl-$\lambda^1$-oxidane (3:1:1) formaldehyde compound) (7.3) R3, R4, R5, R6, R7, R8, R9 and R10 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$alkenyl, carboxyl (—COOH) and their combinations with one another.

In the fourth compound (7), produced from main compound (2); when R1 and R2 are ethyl (—C2H5), R11 and R12 are methyl (—CH3), and in this compound (2-(4-(3,4-dimethoxy-2,5,6-trimethylphenyl)butan-2-yl)-6-ethoxy-3,4,5,8-tetramethyl-7-propoxy-1$\lambda^3$-chromen and methyl-$\lambda^1$-oxidane (3:1:1) formaldehyde compound) (7.4) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$alkenyl, carboxyl (—COOH) and their combinations with one another.

In the fourth compound (7), produced from main compound (2); when R1 is hydroxyl (—OH), R2 is methyl (—CH3), R11 and R12 are methyl (—CH3), and in this compound (2-(4-(3,4-dimethoxy-2,5,6-trimethylphenyl)butan-2-yl)-7-ethoxy-6-hydroperoxy-3,4,5,8-tetramethyl-1$\lambda^3$-chromen and methyl-$\lambda^1$-oxidane (3:1:1) formaldehyde compound) (7.5) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fourth compound (7), produced from main compound (2); when R1 is methyl (—CH3), R2 is hydroxyl (—OH), R11 and R12 are methyl (—CH3), and in this compound (2-(4-(3,4-dimethoxy-2,5,6-trimethylphenyl)butan-2-yl)-6-methoxy-3,4,5,8-tetramethyl-1$\lambda^3$-chromen-7-yl)oxy)methanol and methyl-$\lambda^1$-oxidane (3:1:1) formaldehyde compound) (7.6) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fourth compound (7), produced from main compound (2); when R1 and R2 are hydroxyl (—OH), R11 and R12 are methyl (—CH3), and in this compound (2-(4-(3,4-dimethoxy-2,5,6-trimethylphenyl)butan-2-yl)-6-hydroperoxy-3,4,5,8-tetramethyl-1$\lambda^3$-chromen-7-yl)oxy)methanol and methyl-$\lambda^1$-oxidane (3:1:1)) formaldehyde compound) (7.7) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_1$-$C_6$ alkenyl, carboxyl (—COOH) and their combinations with one another.

In the fourth compound (7), produced from main compound (2); when R1 is hydroxyl(—OH), R2 is ethyl (—C2H5), R11 and R12 are methyl (—CH3), and in this compound (2-(4-(3,4-dimethoxy-2,5,6-trimethylphenyl)butan-2-yl)-6-hydroperoxy-3,4,5,8-tetramethyl-7-propoxy-1$\lambda^3$-chromen and methyl-$\lambda^1$-oxidane (3:1:1) formaldehyde compound) (7.8) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fourth compound (7), produced from main compound (2); when R1 is ethyl(—C2H5), R2 is hydroxyl (—OH), R11 and R12 are methyl (—CH3), and in this compound (2-(4-(3,4-dimethoxy-2,5,6-trimethylphenyl)butan-2-yl)-6-ethoxy-3,4,5,8-tetramethyl-1$\lambda^3$-chromen-7-yl) oxy)methanol and methyl-$\lambda^1$-oxidane (3:1:1) formaldehyde compound) (7.9) R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 and R2 are methyl and in this compound (6-ethoxy 7-methoxy-2,3,4,5,8-pentamethylnaphatehalen-1-ylium (8.1); R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 is ethyl(—C2H5) and R2 is methyl(—CH3), and in this compound (7-methoxy-2,3,4,5,8-pentamethyl-6-propoxynaphatehalen-1-ylium (8.2); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 is methyl(—CH3) and R2 is ethyl(—C2H5), and in this compound (6,7-diethoxy-2,3,4,5,8-pentamethylnaphatehalen-1-ylium (8.3) R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 and R2 are ethyl (—C2H5), and in this compound (7-ethoxy-2,3,4,5,8-pentamethyl-6-propoxynaphatehalen-1-ylium (8.4); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 is hydroxyl (—OH), and R2 is methyl (—CH3) and in this compound (6-(hydroxymethoxy)-7-methoxy-2,3,4,5,8-pentamethylnaphatehalen-1-ylium (8.5); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 is methyl (—CH3), and R2 is hydroxyl (—OH), and in this compound (6-ethoxy-7-hydroperoxy-2,3,4,5,8-pentamethylnaphatehalen-1-ylium (8.6), R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 and R2 are hydroxyl (—OH), and in this compound (7-hydroperoxy-6-(hydroxymethoxy)-2,3,4,5,8-pentamethylnaphatehalen-1-ylium (8.7), R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 is hydroxyl (—OH), and R2 is ethyl (—C2H5), and in this compound (7-ethoxy-6-(hydroxymethoxy)-2,3,4,5,8-pentamethylnaphatehalen-1-ylium (8.8): R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the fifth compound (8), produced from main compound (2); when R1 is ethyl (—C2H5), R2 is hydroxyl (—OH), and in this compound (7-hydroperoxy-2,3,4,5,8-pentamethyl-6-propoxynaphatehalen-1-ylium (8.9); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1, R2, R11 and R12 are methyl (—CH3), and in this compound (1-(3,4-dimethoxy-2,5,6-trimethylphenyl)-3-(6-ethoxy-7-methoxy-3,4,5,8-tetramethyl-1$\lambda^3$-chromen-2-yl)butan-1-one and methyl $\lambda^1$-oxidane (3:1:1) formaldehyde compound (9.1); R3, R4, R5, R6, R7, R8, R9 and R10 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 is ethyl (—C2H5), R2 is methyl (—CH3), R11 and R12 are methyl (—CH3), and in this compound (3-(6,7-diethoxy-3,4,5,8-tetramethyl-1$\lambda^3$-chromen-2-yl)-1-(3,4-dimethoxy-2,5,6-trimethylphenyl)butan-1-one- and hydroxyl-$\lambda^1$-oxidane (3:1:1) formaldehyde compound (9.2); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 is methyl (—CH3), R2 is ethyl (—C2H5), R11 and R12 are methyl (—CH3), and in this compound (1-(3,4-dimethoxy-2,5,6-trimethylphenyl)-3-(7-methoxy-3,4,5,8-tetramethyl-6-propoxy-1$\lambda^3$-chromen-2-yl) butan-1-one and methyl $\lambda^1$-oxidane (3:1:1) formaldehyde compound (9.3); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 and R2 are ethyl (—C2H5), R11 and R12 are methyl (—CH3), and in this compound (1-(3,4-dimethoxy-2,5,6-trimethylphenyl)-3-(7-ethoxy-3,4,5,8-tetramethyl-6-propoxy-1$\lambda^3$-chromen-2-yl)butan-1-one and methyl $\lambda^1$-oxidane (3:1:1) formaldehyde compound (9.4); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 is hydroxyl (—OH), R2 is methyl (—CH3), R11 and R12 are methyl (—CH3), and in this compound (1-(3,4-dimethoxy-2,5,6-trimethylphenyl)-3-(6-(hydroxymethoxy)-7-methoxy-3,4,5,8-tetramethyl-1$\lambda^3$-chromen-2-yl)butan-1-one and methyl $\lambda^1$-oxidane (3:1:1) formaldehyde compound (9.5); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 is methyl (—CH3), R2 is hydroxyl(—OH), R11 and R12 are methyl (—CH3), and in this compound (1-(3,4-dimethoxy-2,5,6-trimethylphenyl)-3-(6-ethoxy-7-hydroperoxy-3,4,5,8-tetramethyl-1$\lambda^3$-chromen-2-yl)butan-1-one- and methyl-$\lambda^1$-oxidane (3:1:1) formaldehyde compound (9.6); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 and R2 are hydroxyl (—OH), R11 and R12 are methyl (—CH3), and in this compound (1-(3,4-dimethoxy-2,5,6-trimethylphenyl)-3-(7-hydroperoxy-6-(hydroxyperoxy)-3,4,5,8-tetramethyl-1$\lambda^3$-chromen-2-yl)butan-1-one and methyl-$\lambda^1$-oxidane (3:1:1) formaldehyde compound (9.7); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 is hydroxyl (—OH), R2 is ethyl (—C2H5), R11 and R12 are methyl (—CH3), and in this compound (1-(3,4-dimethoxy-2,5,6-trimethylphenyl)-3-(7-ethoxy-6-(hydroxyperoxy)-3,4,5,8-tetramethyl-1$\lambda^3$-chromen-2-yl)butan-1-one and methyl $\lambda^1$-oxidane (3:1:1) formaldehyde compound (9.8); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the sixth compound (9), produced from main compound (2); when R1 is ethyl (—C2H5), R2 is hydroxyl (—OH), R11 and R12 are methyl (—CH3), and in this compound (1-(3,4-dimethoxy-2,5,6-trimethylphenyl)-3-(7-hydroperoxy-3,4,5,8-tetramethyl-6-propoxy-1$\lambda^3$-chromen-2-yl)butan-1-one and methyl $\lambda^1$-oxidane (3:1:1) formaldehyde compound (9.9); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2); when R1 and R2 are methyl (—CH3), and in this compound (6,7-diethoxy-2,3,4,5,8-pentamethylnaphatehalen-1-ylium (10.1); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2): when R1 is ethyl (—C2H5) and R2 is methyl (—CH3), and in this compound 7-ethoxy-2,3,4,5,8-pentamethyl-6-propoxynaphatehalen-1-ylium (10.2); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2); when R1 is methyl (—CH3) and R2 is ethyl (—C2H5), and in this compound 6-ethoxy-2,3,4,5,8-pentamethyl-7-propoxynaphatehalen-1-ylium (10.3); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2); when R1 and R2 are ethyl (—C2H5), and in this compound 2,3,4,5,8-pentamethyl-6,7-dipropoxynaphatehalen-1-ylium (10.4); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H1-15), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2); when R1 is hydroxyl (—OH) and R2 is methyl (—CH3), and in this compound 7-ethoxy-6-(hydroxymethoxy)-2,3,4,5,8-pentamethylnaphatehalen-1-ylium (10.5); R3, R4, R5, R6 and R7 can be; hydrogen, (—H), hydroxyl, (—CL), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2); when R1 is methyl (—CH3) and R2 is hydroxyl (—OH), and in this compound 6-ethoxy-7-(hydroxymethoxy)-2,3,4,5,8-pentamethylnaphatehalen-1-ylium (10.6); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2): when R1 and R2 are hydroxyl (—OH), and in this compound 6,7-bis(hydroxymethoxy)-2,3,4,5,8-pentamethylnaphatehalen-1-ylium (10.7) R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2): when R1 is hydroxyl(—OH) and R2 is ethyl (—C2H5), and in this compound 6-(hydroxymethoxy)-2,3,4,5,8-pentamethyl-7-propoxynaphatehalen-1-ylium (10.8); R3, R4, R5, R6 and R7 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the seventh compound (10), produced from main compound (2); when R1 is ethyl (—C2H5) and R2 is hydroxyl(—OH), and in this compound 7-(hydroxymethoxy)-2,3,4,5,8-pentamethyl-6,7-propoxynaphatehalen-1-ylium (10.9); R3, R4, R5, R6 and R7 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1, R2, R11 and R12 are methyl (—CH3), and in this compound (3-(6,7-diethoxy-3,4,5,8-tetramethyl-1$\lambda^3$-chromen-2-yl)-1-(3,4-dimethoxy-2,5,6-trimethylphenyl)butan-1-one- and methyl-$\lambda^1$-oxidane (3:1:1) formaldehyde compound (11.1); R3, R4, R5, R6, R7, R8, R9 and R10 can be: hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1 is ethyl (—C2H5), R2 is methyl (—CH3) R11 and R12 are methyl (—CH3) and in this compound (1-(3,4-dimethoxy-2,5,6-trimethylphenyl)-3-(7-ethoxy,3,4,5,8-tetramethyl-6-propoxy-1$\lambda^3$-chromen-2-yl)butan-1-one-methyl-$\lambda^1$-oxidane (3:1:1) formaldehyde compound (11.2); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2): when R1 is methyl (—CH3), R2 is ethyl (—C2H5), R11 and R12 are methyl (—CH3) and in this compound (1-(3,4-dimethoxy-2,5,6-trimethylphenyl)-3-(6-ethoxy-3,4,5,8-tetramethyl-7-propoxy-1$\lambda^3$-chromen-2-yl)butan-1-one-methyl-$\lambda^1$-oxidane (3:1:1) formaldehyde compound (11.3); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R l and R2 are ethyl (—C2H5), R11 and R12 are methyl (—CH3) and in this compound (1-(3,4-dimethoxy-2,5,6-trimethylphenyl)-3-(0,3,4,5,8-tetramethyl-6,7-dipropoxy-1$\lambda^3$-chromen-2-yl)butan-1-one-methyl-$\lambda^1$-oxidane (3:1:1) formaldehyde compound (11.4); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1 is hydroxyl (—OH), R2 is methyl (—CH3), R11 and R12 are methyl (—CH3) and in this compound (1-(3,4-dimethoxy-2,5,6-trimethylphenyl)-3-(7-ethoxy-6-(hydroxyperoxy)-3,4,5,8-tetramethyl-1$\lambda^3$-chromen-2-yl)butan-1-one and methyl $\lambda^1$-oxidane (3:1:1) formaldehyde compound (11.5); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1 is methyl (—CH3), R2 is hydroxyl (—OH), R11 and R12 are methyl (—CH3) and in this compound (1-(3,4-dimethoxy-2,5,6-trimethylphenyl)-3-(6-ethoxy-7-(hydroxymethoxy)-3,4,5,8-tetramethyl-1$\lambda^3$-chromen-2-yl)butan-1-one-and-methyl-$\lambda^1$-oxidane (3:1:1) formaldehyde compound (11.6); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1 and R2 are hydroxyl (—OH), R11 and R12 are methyl (—CH3) and in this compound (3-(6,7-bis (hydroxymethoxy)-3,4,5,8-tetramethyl-1$\lambda^3$-chromen-2-yl)-1-(3,4-dimethoxy-2,5,6-trimethylphenyl)butan-1-one-and-methyl-$\lambda^1$-oxidane (3:1:1) formaldehyde compound (11.7); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1 is hydroxyl (—OH), R2 is ethyl (—C2H5), R1 and R12 are methyl (—CH3) and in this compound 1-(3,4-dimethoxy-2,5,6-trimethylphenyl)-3-(6-(hydroxymethoxy)-(3,4,5,8-tetramethyl-7-propoxy-1$\lambda^3$-chromen-2-yl)butan-1-one-and-methyl-$\lambda^1$-oxidane (3:1:1) formaldehyde compound (11.8); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

In the eight compound (11), produced from main compound (2); when R1 is ethyl (—C2H5), R2 is hydroxyl (—OH), R11 and R12 are methyl (—CH3) and in this compound (1-(3,4-dimethoxy-2,5,6-trimethylphenyl)-3-(7-(hydroxymethoxy)-(3,4,5,8-tetramethyl-6-propoxy-1$\lambda^3$-chromen-2-yl) butan-1-one-and-methyl-$\lambda^1$-oxidane (3:1:1) formaldehyde compound (11.9); R3, R4, R5, R6, R7, R8, R9 and R10 can be; hydrogen, (—H), hydroxyl, (—OH), fluoride (—F), chloride, (—CL), bromide (—Br), iodine (—I), methyl (—CH3), ethyl (—C2H5), amino (—NH2), nitro (—NO2), $C_3$-$C_6$ cycloalkenyl, $C_1$-$C_6$ alkoxide, $C_1$-$C_6$ alkyl, $C_1$-$C_6$ fluoroalkyl, $C_2$-$C_6$ alkenyl, carboxyl (—COOH) and their combinations with one another.

The invention claimed is:

1. A compound having the following formula:

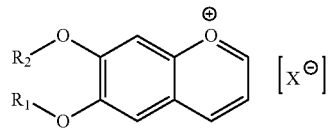

wherein
each $R_1$ and $R_2$ are independently selected from the group consisting of —H, methyl, ethyl, propyl, hydroxymethyl, hydroxyethyl, and hydroxypropyl; and
X is a counter anion selected from the group consisting of perchlorate, hexafluorophosphate, and tetrafluoroborate.

2. The compound of claim 1, wherein each $R_1$ and $R_2$ are independently selected from the group consisting of —H, methyl, ethyl, propyl, hydroxymethyl, and hydroxyethyl.

3. The compound of claim 1, wherein each $R_1$ and $R_2$ are independently selected from the group consisting of —H, methyl, ethyl, propyl, and hydroxymethyl.

4. The compound of claim 1, wherein each $R_1$ and $R_2$ are independently selected from the group consisting of methyl, ethyl, and propyl.

5. The compound of claim 1, wherein the counter anion X is perchlorate.

6. The compound of claim 1, which is selected from the group consisting of:

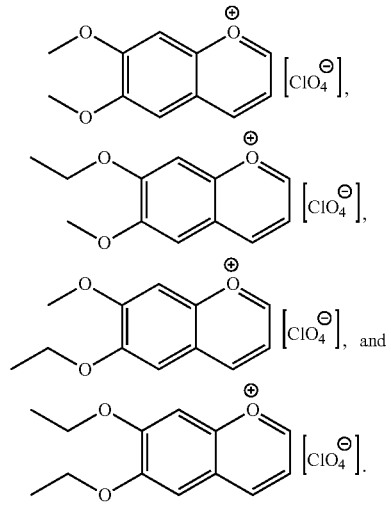

7. A pharmaceutical composition comprising a compound having the following formula:

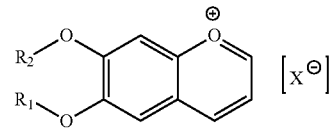

wherein
each $R_1$ and $R_2$ are independently selected from the group consisting of —H, methyl, ethyl, propyl, hydroxymethyl, hydroxyethyl, and hydroxypropyl; and
X is a counter anion selected from the group consisting of perchlorate, hexafluorophosphate, and tetrafluoroborate.

8. The pharmaceutical composition of claim 7, wherein the compound is selected from the group consisting of:

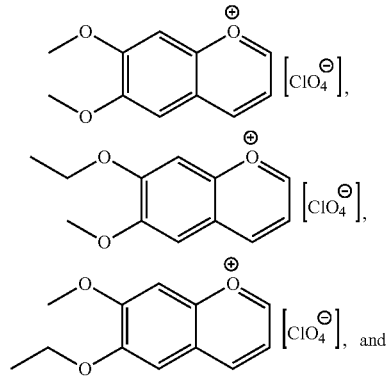

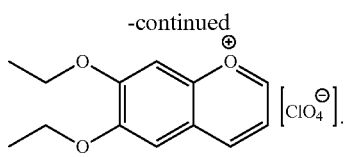

9. The pharmaceutical composition of claim 7, wherein each $R_1$ and $R_2$ are independently selected from the group consisting of —H, methyl, ethyl, propyl, hydroxymethyl, and hydroxyethyl.

10. The pharmaceutical composition of claim 7, wherein each $R_1$ and $R_2$ are independently selected from the group consisting of —H, methyl, ethyl, propyl, and hydroxymethyl.

11. The pharmaceutical composition of claim 7, wherein each $R_1$ and $R_2$ are independently selected from the group consisting of methyl, ethyl, and propyl.

12. The pharmaceutical composition of claim 7, wherein the counter anion X is perchlorate.

13. A method for treating fibrosis comprising administering to a subject in need thereof a therapeutically effective amount of a compound having the following formula:

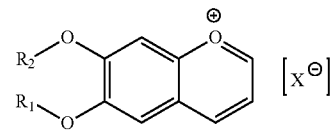

wherein
  each $R_1$ and $R_2$ are independently selected from the group consisting of —H, methyl, ethyl, propyl, hydroxymethyl, hydroxyethyl, and hydroxypropyl; and
  X is a counter anion selected from the group consisting of perchlorate, hexafluorophosphate, and tetrafluoroborate.

14. The method of claim 13, wherein the fibrosis is lung fibrosis.

15. The method of claim 13, wherein the fibrosis is idiopathic pulmonary fibrosis (IPF).

16. The method of claim 13, wherein the fibrosis is liver fibrosis.

17. The method of claim 13, wherein the fibrosis is non-alcoholic steatohepatitis (NASH).

* * * * *